US006962675B2

(12) United States Patent
Lewis et al.

(10) Patent No.: US 6,962,675 B2
(45) Date of Patent: Nov. 8, 2005

(54) USE OF SPATIOTEMPORAL RESPONSE BEHAVIOR IN SENSOR ARRAYS TO DETECT ANALYTES IN FLUIDS

(75) Inventors: Nathan S. Lewis, La Canada, CA (US); Michael S. Freund, Altadena, CA (US); Shawn M. Briglin, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 310 days.

(21) Appl. No.: 10/214,794

(22) Filed: Aug. 7, 2002

(65) Prior Publication Data

US 2002/0192117 A1 Dec. 19, 2002

Related U.S. Application Data

(62) Division of application No. 09/568,784, filed on May 10, 2000, now Pat. No. 6,455,319.
(60) Provisional application No. 60/140,027, filed on Jun. 16, 1999, and provisional application No. 60/133,318, filed on May 10, 1999.

(51) Int. Cl.[7] .......................... G01N 7/00; G01N 27/00; G01N 21/00; G01N 31/00; G01N 33/00
(52) U.S. Cl. .......................... 422/83; 422/50; 422/68.1; 422/83; 422/98; 422/82.01; 422/82.02; 436/121; 436/151; 73/1.02; 73/23.2; 73/23.34
(58) Field of Search .................. 422/68.1, 50, 82.02, 422/83, 98, 82.01; 436/121, 151; 73/23.2, 23.34, 1.02

(56) References Cited

U.S. PATENT DOCUMENTS

| | | | |
|---|---|---|---|
| 3,677,071 A | 7/1972 | Martin | |
| 4,172,721 A | 10/1979 | Byrne | |
| 4,225,410 A | 9/1980 | Pace | |
| 4,349,664 A | 9/1982 | Matsumura et al. | |
| 4,424,487 A | 1/1984 | Lauffer | |

(Continued)

FOREIGN PATENT DOCUMENTS

| | | |
|---|---|---|
| EP | 0 632 268 A1 * | 1/1995 |
| EP | 0 717 418 A2 | 6/1996 |
| EP | 0 878 711 A1 | 11/1998 |
| JP | 62-257968 | 11/1987 |
| JP | 63-120733 | 5/1988 |

(Continued)

OTHER PUBLICATIONS

Baldacci, et al., "Discrimination of Wine Using Taste and Smell Sensors", Sensors and Materials, vol. 10, No. 3, pp. 185–200 (1998).

Bodenhofer, et al., "Chiral Discrimination By Simple Gas Sensors", Transducers, 1997 International Conference on Solid–State Sensors and Actuators, Digest of Technical Papers, Transducers 97, chicago, IL, Jun. 16–19, 1997, vol. 2, pp. 1391–1394IEEE.

(Continued)

Primary Examiner—Jill Warden
Assistant Examiner—Brian Sines
(74) Attorney, Agent, or Firm—Fish & Richardson P.C.

(57) ABSTRACT

Methods, systems and sensor arrays are provided implementing techniques for detecting an analyte in a fluid. The techniques include providing a sensor array including at least a first sensor and a second sensor in an arrangement having a defined fluid flow path, exposing the sensor array to a fluid including an analyte by introducing the fluid along the fluid flow path, measuring a response for the first sensor and the second sensor, and detecting the presence of the analyte in the fluid based on a spatio-temporal difference between the responses for the first and second sensors.

47 Claims, 14 Drawing Sheets

U.S. PATENT DOCUMENTS

| | | |
|---|---|---|
| 4,644,154 A | 2/1987 | Brogardh et al. |
| 4,674,320 A | 6/1987 | Hirschfeld |
| 4,719,423 A | 1/1988 | Vinegar et al. |
| 4,772,559 A | 9/1988 | Preti et al. |
| 4,818,348 A * | 4/1989 | Stetter ........................ 205/780 |
| 4,884,435 A * | 12/1989 | Ehara ........................ 73/23.34 |
| 4,911,801 A | 3/1990 | Pons |
| 4,914,608 A | 4/1990 | LeBihan et al. |
| 4,927,502 A | 5/1990 | Reading et al. |
| 4,946,562 A | 8/1990 | Guruswamy |
| 5,080,131 A * | 1/1992 | Ono et al. ............. 137/599.11 |
| 5,159,829 A | 11/1992 | Mayer et al. |
| 5,177,994 A * | 1/1993 | Moriizumi et al. ........ 73/23.34 |
| 5,212,447 A | 5/1993 | Paltiel |
| 5,215,820 A | 6/1993 | Hosokawa et al. |
| 5,217,692 A | 6/1993 | Rump et al. |
| 5,225,110 A | 7/1993 | Kathirgamanathan |
| 5,246,846 A | 9/1993 | Pittner et al. |
| 5,250,264 A | 10/1993 | Walt et al. |
| 5,253,329 A | 10/1993 | Villarreal et al. |
| 5,278,501 A | 1/1994 | Guilfoyle |
| 5,286,414 A | 2/1994 | Kampf et al. |
| 5,302,274 A | 4/1994 | Tomantachger et al. |
| 5,335,555 A | 8/1994 | Guizot et al. |
| 5,352,574 A | 10/1994 | Guiseppi-Elie |
| 5,407,699 A | 4/1995 | Myers |
| 5,415,893 A | 5/1995 | Wiersma et al. |
| 5,417,100 A | 5/1995 | Miller et al. |
| 5,425,869 A | 6/1995 | Noding et al. |
| 5,466,348 A | 11/1995 | Holm-Kennedy |
| 5,469,369 A | 11/1995 | Rose-Pehrsson et al. |
| 5,498,372 A | 3/1996 | Hedges |
| 5,505,093 A | 4/1996 | Giedd et al. |
| 5,519,147 A | 5/1996 | Swager et al. |
| 5,536,473 A | 7/1996 | Monkman et al. |
| 5,571,401 A | 11/1996 | Lewis et al. |
| 5,591,898 A | 1/1997 | Mayer |
| 5,627,329 A | 5/1997 | Krishnan et al. |
| 5,653,939 A | 8/1997 | Hollis et al. |
| 5,674,752 A | 10/1997 | Buckley et al. |
| 5,675,070 A * | 10/1997 | Gelperin ..................... 73/23.34 |
| 5,698,089 A | 12/1997 | Lewis et al. |
| 5,705,265 A | 1/1998 | Clough et al. |
| 5,756,879 A | 5/1998 | Yamagishi et al. |
| 5,766,934 A | 6/1998 | Guiseppi-Elie |
| 5,788,833 A | 8/1998 | Lewis et al. |
| 5,801,297 A * | 9/1998 | Mifsud et al. .............. 73/23.34 |
| 5,804,100 A | 9/1998 | Angelopoulos et al. |
| 5,807,701 A * | 9/1998 | Payne et al. .................. 435/34 |
| 5,832,411 A * | 11/1998 | Schatzmann et al. ......... 702/23 |
| 5,841,021 A | 11/1998 | De Castro et al. |
| 5,846,744 A | 12/1998 | Athey et al. |
| 5,876,577 A | 3/1999 | McAleer et al. |
| 5,879,827 A | 3/1999 | Debe et al. |
| 5,891,398 A | 4/1999 | Lewis et al. |
| 5,911,872 A | 6/1999 | Lewis et al. |
| 5,913,235 A | 6/1999 | Silenius et al. |
| 5,948,684 A | 9/1999 | Weigl et al. |
| 5,951,846 A | 9/1999 | Lewis et al. |
| 5,958,787 A | 9/1999 | Schonfeld et al. |
| 5,959,191 A | 9/1999 | Lewis et al. |
| 5,980,723 A | 11/1999 | Runge-Marchese et al. |
| 6,007,775 A | 12/1999 | Yager |
| 6,010,616 A | 1/2000 | Lewis et al. |
| 6,013,229 A | 1/2000 | Lewis et al. |
| 6,017,440 A | 1/2000 | Lewis et al. |
| 6,023,163 A | 2/2000 | Flaum et al. |
| 6,028,608 A | 2/2000 | Jenkins |
| 6,040,189 A * | 3/2000 | Buehler ...................... 436/151 |
| 6,042,788 A * | 3/2000 | De Wit et al. ............ 422/82.02 |
| 6,046,054 A * | 4/2000 | McGeehin et al. .......... 436/121 |
| 6,085,576 A * | 7/2000 | Sunshine et al. .......... 73/29.01 |
| 6,093,308 A | 7/2000 | Lewis et al. |
| 6,103,033 A | 8/2000 | Say et al. |
| 6,134,461 A | 10/2000 | Say et al. |
| 6,134,950 A | 10/2000 | Forster et al. |
| 6,170,318 B1 | 1/2001 | Lewis |
| 6,200,814 B1 | 3/2001 | Malmqvist et al. |
| 6,234,004 B1 | 5/2001 | Revsbech et al. |
| 6,244,096 B1 * | 6/2001 | Lewis et al. ................. 73/23.2 |
| 6,290,911 B1 | 9/2001 | Lewis et al. |
| 6,305,214 B1 | 10/2001 | Schattke et al. |
| 6,315,956 B1 | 11/2001 | Foulger |
| 6,350,369 B1 | 2/2002 | Lewis et al. |
| 6,431,016 B1 * | 8/2002 | Payne ...................... 73/864.73 |

FOREIGN PATENT DOCUMENTS

| | | |
|---|---|---|
| JP | 63-308807 | 12/1988 |
| JP | 11-94784 | 4/1999 |
| WO | WO 86/01599 | 3/1986 |
| WO | WO 90/09027 | 8/1990 |
| WO | WO 94/24561 | 10/1994 |
| WO | WO 95/08113 | 3/1995 |
| WO | WO 96/07901 | 3/1996 |
| WO | WO 99/00663 | 1/1999 |
| WO | WO 99/08105 | 2/1999 |
| WO | WO 99/40423 | 8/1999 |
| WO | WO 99/47905 | 9/1999 |
| WO | WO 99/53287 | 10/1999 |
| WO | WO 99/53300 | 10/1999 |
| WO | WO 99/61902 | 12/1999 |
| WO | WO 99/66304 | 12/1999 |
| WO | WO 99/67627 | 12/1999 |
| WO | WO 00/00808 | 1/2000 |
| WO | WO 00/26638 | 5/2000 |
| WO | WO 00/33062 | 6/2000 |

OTHER PUBLICATIONS

Bodenhofer et al., "Performances of Mass–Sensitive Devices for Gas Sensing: Thickness Shear Mode and Surface Acoustic Wave Transducers", *Anal. Chem.*, vol. 68, No. 13, pp. 2210–2218 (Jul. 1, 1996).

Breheret et al., "On–line differentiation of mushrooms aromas by combined Headspace/multi–odour gas sensors devices", *Bioflavour 95*, Dijon, France (Les Colloques, No. 75), pp. 103–107, (Feb. 14–17, 1995).3.

Bruschi et al., "Gas sensing with conducting polymer thin film resistors obtained from commercial photoresist patterns", *Proceedings of the First Italian Conference*, (1996), pp. 69–73.

Butterworth, et al., "Zeta Potential measurements on Conducting Polymer–Inorganic Oxide Nanocomposite Particles", *Journal of Colloid and Interface Science*, vol. 174, pp. 510–517, (1995).

Casella, et al., "Copper dispersed into polyaniline films as an amperometric sensor in alkaline solutions of amino acids and polyhydric compounds", *Analytics Chimica Acta*, vol. 335, pp. 217–225, (1996).

Chandiok et al., "Screening for bacterial vaginosis: a novel application of artificial nose technology", *J. Clin. Pathol.*, vol. 50, pp. 790–791 (1997).

Forsyth, et al., "Dielectric properties of conductive composites at microwave frequencies", *New Horizons for Materials*, 2995, pp. 279–285 (1995).

Jiang, et al., "Preparation and Properties of Organic Polymer Sub–Micrometer Function Films", *Electrets*, 1996, 9$^{th}$ International Symposium on Shanghai, China, Sep. 25–30, 196, NY, pp. 678–683.

Laranjeira et al., "A conductimetric system based on polyaniline for determination of ammonia in fertilizers", *Analytical Letters*, vol. 30, No. 12, pp. 2189–2209 (1997).

Lefebre, et al., "Chemical Synthesis, Characterization, and Electrochemical Studies of Poly (3,4,–ethylenedioxythiophene)Poly(styrene–4–sulfonate) Composites", *Chem. Mater.*, vol. 11, No. 2, pp. 262–268 (1999).

Luinge, et al., "Trace–level identity confirmation from infrared spectra by library searching and artificial neural networks", Analytica Chimica Acta, vol. 345, pp. 173,–184, 1997.

Meister et al., "Polymer–Oxide–Silicon–Field–Effect–Transistor (POSFET) as sensor for gases and vapors", *Electrochemical Society Proceedings*, vol. 97–9, pp 16–22.

Moy et al., "Transient signal modelling for fast odour classification", *Bioflavour 95*, Dijon, France, (Les Colloques, No. 75), pp. 55–58, (Feb. 14–17, 1995).

Neaves et al., "A new generation of integrated electronic noses", *Sensors and Actuators*, B 26–27, pp. 223–231 (1995).

Partch, et al., "Conducting Polymer Composites", American Chemical Society, pp. 368–386 (1992).

Paulsson, et al., "Breath alcohol, multi sensor arrays and electronic noses", *SPIE*, vol. 2932, pp. 84–90 (Mar. 1997).

Preti, "Analysis of lung air from patients with bronchogenic carcinoma and controls using gas chromatography–mas spectrometry", *Journal of Chromatography*, vol. 432, pp 1–11 (1988).

Rajeshwar, et al., "Polypyrrole composits containing platinum or carbon black: from synthesis to novel applications", *Polymer Preprints, American Chemical Society*, vol. 35, No. 1, pp. 234–235, Mar., 1994).

Simenhoff, et al. "Biochemical profile of uremic breath", *The New England Journal of Medicine*, vol. 297, No. 3, pp. 132–135 (Jul. 21, 1977).

Stussi, et al., "Chemoresistive conducting polymer–based odour sensors: influence of thickness changes on their sensing properties", *Sensors and Actuators*, vol. B43, pp. 180–185, (1997).

Thackeray, et al., "Chemically Responsive Microelectrochemical Devices Based on Platinized Poly (3–methylthiophene): Variation in conductivity with Variation in Hydrogen, Oxygen, or pH in Aqueous solution", Feb. 14–17, 1995,*J. Phys. Chem.* Feb. 14–17, 1995, vol. 90, No. 25, pp. 6674–6679 (Nov. 25, 1986).

Tourillon, et al., "Dispersive X–Ray Spectroscopy for Time–Resolved In Situ Observatin of Electrochemical Inclusion of Metallic Clusters within a conducting polymer", *Physical Review Letters*, vol. 57, No. 5, pp. 603–606 (Aug. 4, 1986).

Udrea et al., "Design of a silicon microsensor array device for gas analysis", *Microelectronics Journal*, vol. 27, No. 6, pp. 449–457 (1996).

Wampler, "Composites of Polypyrrole and Carbon Black. 2. Electrosynthesis, Characterization, and Influence of Carbon Black Characteristics", *Chem. Mater.* vol. 7, No. 3, pp. 585–592 (1995).

Veciana–Nogues, et al., "Biogenic Amines as Hygienic Quality Indicators of Tuna, Relationships with Microbial Counts, ATP–Related Compounds, Volatile Amines and Organoleptic Changes", *J. Agric. Food Chem.*, vol. 45, No. 6, pp. 2036–2041 (1997).

Yamato et al., "A new method for dispersing palladium icroparticles in conducting polymer films and its application to biosensors", *Synthetic Metals*, vol. 87, pp. 231–236, (1997).

Wehrens, et al., "Calibration of an array of voltammetric microelectrodes", *Analytica chimica Acta.*, No. 334, pp. 93–101, 1996.

Williams, et al., "Resolving combustible gas mixtures using gas sensitive resistors with arrays of electrodes", *J. Chem. Soc., Faraday Trans.*, vol. 92, No. 22, pp. 4497–4504, 1996.

Shurmer, et al., "Integrated Arrays of Gas Sensors Using Conducting Polymers with Molecular–Sieves", *Sensors and Actuators*, vol. 4, pp. 29–33, 1991.

Slater, et al., "Examination of Ammonia Poly(pyrrole) Interactions by Piezoelectric and Conductivity Measurements", *Analyst*, vol. 116, pp. 1125–1130, Nov., 1991.

Grate, et al., "Acoustic–wave microsensors", *Anal. Chem.*, vol. 65, No. 22, pp. A987–A996, Nov. 15, 1993.

Grate, et al., "Acoustic–wave microsensors", *Anal. Chem.*, vol. 65, No. 21, pp. A940–A948, Nov. 1, 1993.

Cornila, et al., "Capacitive sensors in CMOS technology with polymer coating", *Sensors and Actuators*, vol. 25, pp. 357–361, 1995.

Johnson, et al., "Identification of Multiple Analytes Using an Optical Sensor Array and Pattern Recognition Neural Networks", *Anal. Chem.*, vol. 69, No. 22, pp. 4641–4648, Nov. 15, 1997.

Dickinson, et al., "A chemical–detecting system based on a cross–reactive optical sensor array", *Nature*, vol. 382, pp. 697–700, Aug., 1996.

White, et al., "Rapid Analyte Recognition in a Device Based on Optical Sensors and the Olfactory System", *Anal. Chem.*, vol. 68, No. 13, pp. 2191–2202, Jul. 1, 1996.

Harsanyi, "Polymer FIlms in Sensor Applications", Technomic Publishing Co., Inc., Lancaster, 1995.

Albert, et al., "Cross–Reactive Chemical Sensor Arrays", *Chem. Rev.*, vol. 100, No. 7, pp. 2595–2626, 2000.

Doleman, et al., "Use of Compatible Polymer Blends to Fabricate Arrays of Carbon Black–Polymer Composite Vapor Detectors", *Anal. Chem.*, vol. 70, No. 13, pp. 2560–2564, 1998, Jul. 1, 1998.

Benes, et al., "Sensors based on piezoelectric resonators", *Sensors and Actuators*, vol. A48, No. 1, pp. 1–21, 1995.

Grate, et al., "Surface Acoustic–Wave Vapor Sensors Based on Resonator Devices", *Anal. Chem.*, vol. 63, No. 17, pp. 1719–1727, Sep. 1, 1991.

Briglin, et al., Progress in Use of Carbon Black–Polymer Composite Vapor Detector Arrays for Land Mine Detection, *Proc. SPIE–Int. Eng.*, vol. 4038, Part One of Two Parts, pp. 530–538, Apr. 24–28, 2000, Orlando, Florida, USA.

Wilmshurt, "Signal recovery from noise in electronic instrumentation", Adam Hilger Ltd., Boston, pp. 60–68, 1985.

Larry, et al., "Thick–Film Technology: An introduction to the Materials", IEEE Transactions on Components, Hybridss, and Manufacturing Technology, vol. CHMT–3, No. 2, pp. 211–225, Jun., 1980.

Weissman, et al., "1/f noise and other slow, nonexponential kinetics in condensed matter", *Rev. Mod. Phys.*, vol. 60, No. 2, pp. 537–571, Apr., 1988.

Dzidzic, et al., "1/f noise in polymer thick–film resistors", *J. Phys. D–Appl. Phys.*, vol. 31, pp. 2091–2097, 1998.

Scofield, et al., "Exclusion of temperature fluctuations as the source of 1/f noise in metal films", *Phys. Rev.*, vol. 24, No. 12, pp. 7450–7453, Dec. 15, 1981.

Fu, et al., "Electrical Characteristics of Polymer Thick Film Resistors, Part I: Experimental Results", *IEEE Transactions on Components, Hybrids, and Manufacturing Technology*, vol. 4, No. 3, pp. 283–288, Sep., 1981.

Deen, et al., "Low frequency noise in heavily doped polysilicon thin film resistors", *J. Vac. Sci. Technol.*, vol. 16, No. 4, pp. 1881–1884, Jul./Aug., 1998.

Severin, et al., "Relationships among Resonant Frequency Changes on a Coated Quartz Crystal Microbalance, Thickness Changes, and Resistance Repsonses of Polymer–Carbon Black Composite Chemiresistors", *Anal. Chem.*, vol. 72, No. 9, pp. 2008–2015, May 1, 2000.

Peled, et al., "1/f Noise in Bismuth Ruthenate Based Thick–Film Resistors", *IEEE Transactions on Components, Packaging, and Manufacturing Technology*, Part A20, vol. 20, No. 3, pp. 355–360, Sep., 1997.

Horowitz, et al., "The Art of Electronics", $2^{nd}$, ed., Cambridge University Press, Cambridge, 1989.

Lu, "Applications of Piezoelectric Quartz Crystal Microbalances", pp. 19–61, Elsevier, New York, 1984.

Buttry, "Electroanalytical Chemistry; a Series of Advances", Marcel Dekker, New York, 1991.

Doleman, et al., "Trends in odor intensity for human and electronic noses: Relative roles of odorant vapor pressure vs. molecularly specific odorant binding", *Proc. Natl. Acadm. Sci.*, vol. 95, pp. 5442–5447, May, 1998.

Severin, et al. "An Investigation of the Concentration Dependence and Response to Analyte Mixtures of Carbon Black/Insulating Organic Polymer Composite Vapor Detectors", *Anal. Chem.*, vol. 72, No. 4, pp. 658–668, Feb. 15, 2000.

Patrash, et al., "Characterization of Polymeric Surface–Acoustic Wave Sensor Coatings and Semiempirical Models of Sensor Response to Organic Vapors", *Anal. Chem.*, vol. 65, No. 15, pp. 2055–2066, Aug. 1, 1993.

Zellers, et al., "Establishing a Limit of Recognition for a Vapor Sensor Array", *Anal. Chem.*, vol. 70, No. 19, pp. 4191–4201, Oct. 1, 1998.

LaGrone, et al., Landmine Detection by Chemical Signature: Detection of Vapors of Nitroaromatic Compounds by Fluorescence Quenching of Novel Polymer Materials, *Proc. SPIE–Int. Opt. Eng.*, vol. 3710. pp. 409–420, Apr. 5–9, 1999, Orlando, Florida, USA.

George, et al., "Progress on Determining the Vapor Signature of a Buried Land Mine", *Proc. SPIE–Int. Opt. Eng.*, vol. 3710, pp. 258–269, Apr. 5–9, 1999, Orlando, Florida, USA.

Sobel, et al., "Olfaction—the world smells different to each nostril", *Nature*, vol. 402, pp. 35, Nov. 4, 1999.

deLacy Costello et al., "Novel Composite Organic–Inorganic Semiconductor Sensors for the Quantitative Detection ofTarget Organic Vapours", *J. Mater. Chem.*, vol. 6, No. 3, pp. 289–294 (1996).

Dickinson et al., "Generating Sensor Diversity Through Combinatorial Polymer Synthesis", *Anal. Chem.*, vol. 69, pp/ 3413–3418 (1997).

Doleman et al., "Quantitative Study of the Resolving Power of Arrays of Carbon Black–Polymer Composites in Various Vapor–Sensing Tasks", *Anal. Chem.*, vol. 70, pp. 4177–4190 (1998).

Domansky et al., "Development and Calibration of Field–Effect Transistor–Based Sensor Array for Measurement of Hydrogen and Ammonia Gas Mixtures in Humid Air", *Anal. Chem.*, vol. 70, pp. 473–481 (1998).

Freund and Lewis, "A Chemically Diverse Conducting Polymer–Based 'Electronic Nose'", *Proc. Nat'l Acad. Sci. USA*, vol. 92, pp. 2652–2656 (1995).

J. Lipman, "E–Noses Nose Out Traditional Odor–Detection Equipment", *EDN Magazine*, (Dec., 1998).

Lonergan et al., "Array–Based Vapor Sensing Using Chemically Sensitive, Carbon Black–Polymer Resistors", *Chem. Mater.*, vol. 8, 2298–2312 (1996).

Pearce et al., "Electronic Nose for Monitoring the Flavour of Beers", *Analyst*, vol. 118, pp. 371–377 (1993).

Slater et al., "Multi–layer Conducting Polymer Gas Sensor Arrays for Olfactory Sensing", *Analyst*, vol. 118, pp. 379–384 (1993).

* cited by examiner

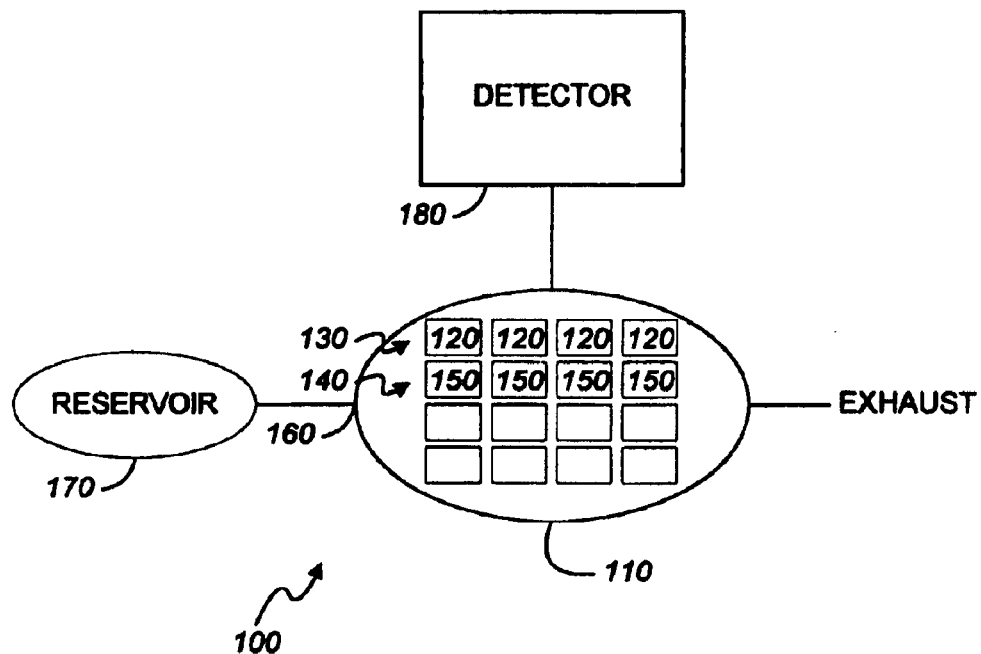
FIG._1
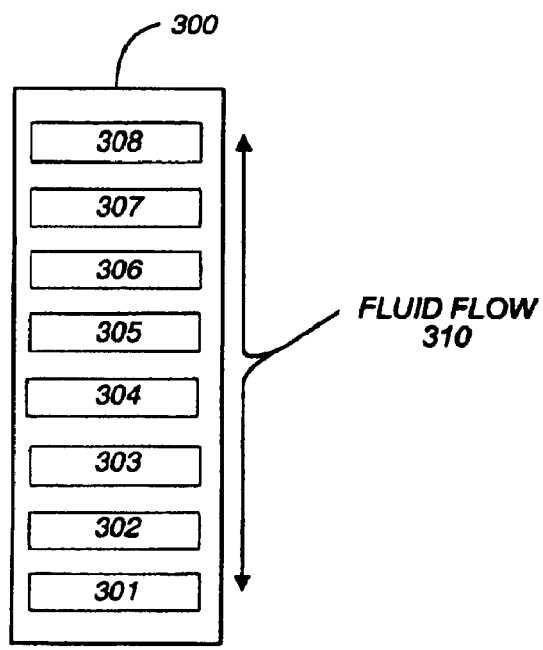
FIG._3

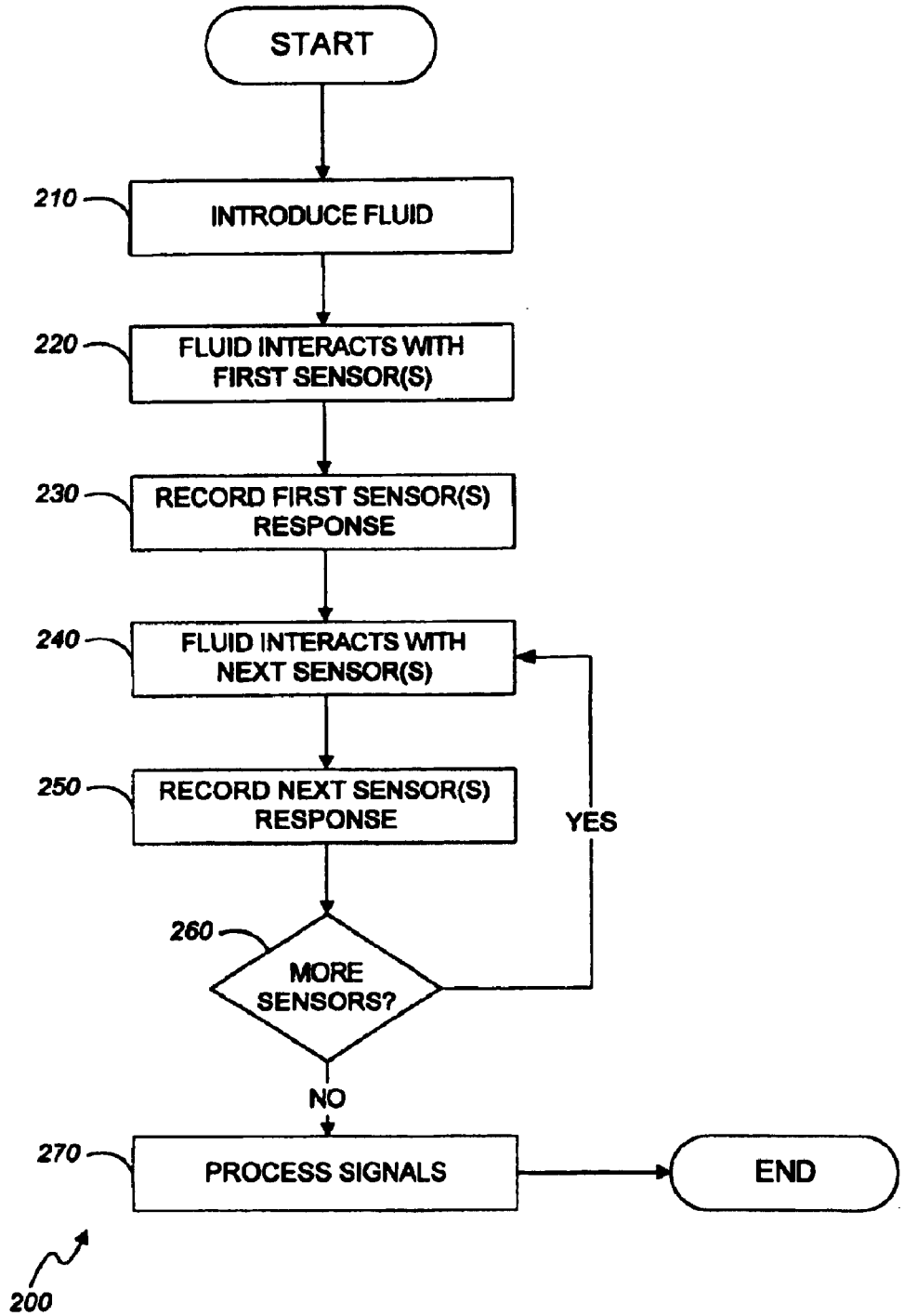
FIG._2

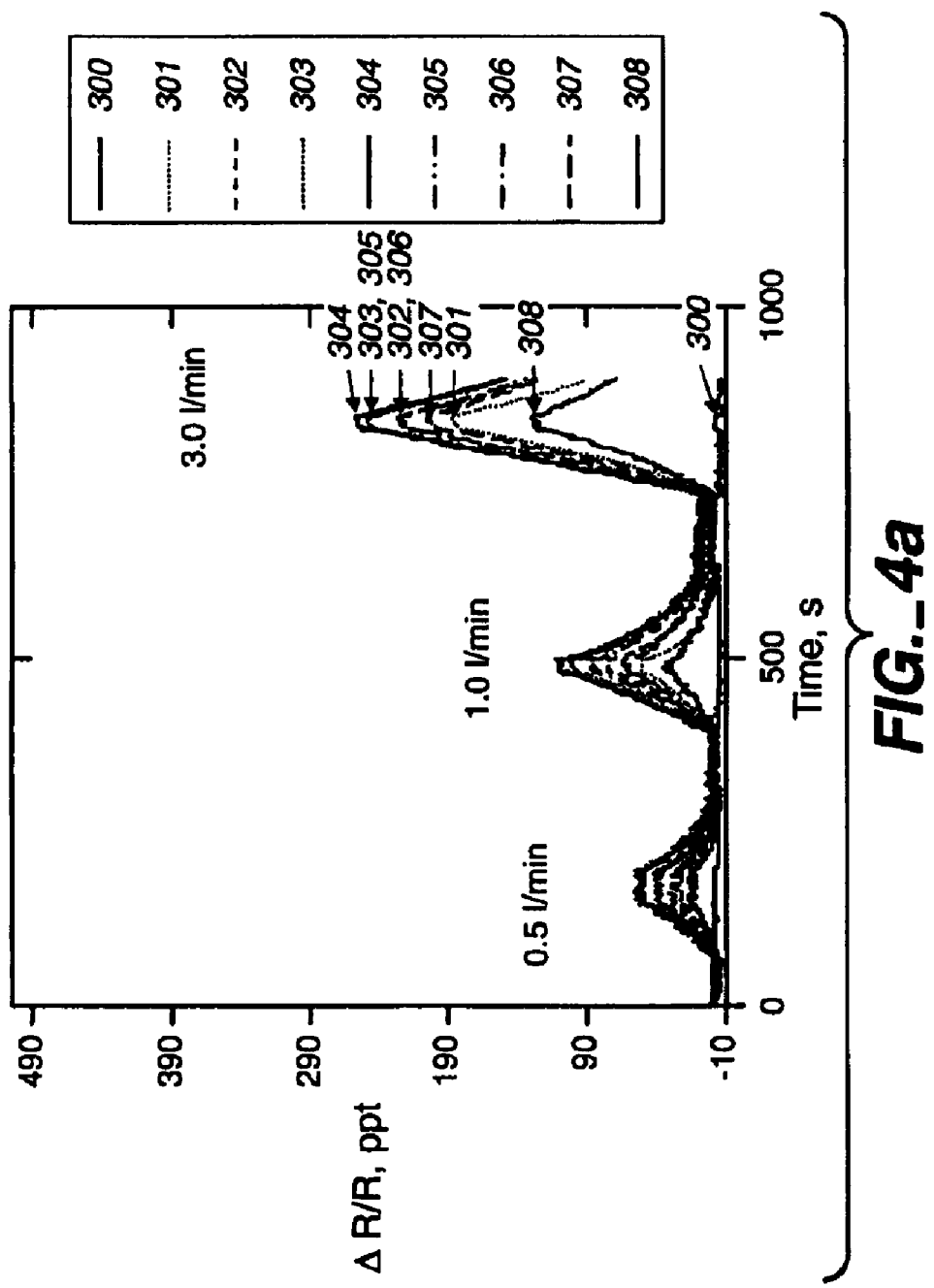
FIG._4a

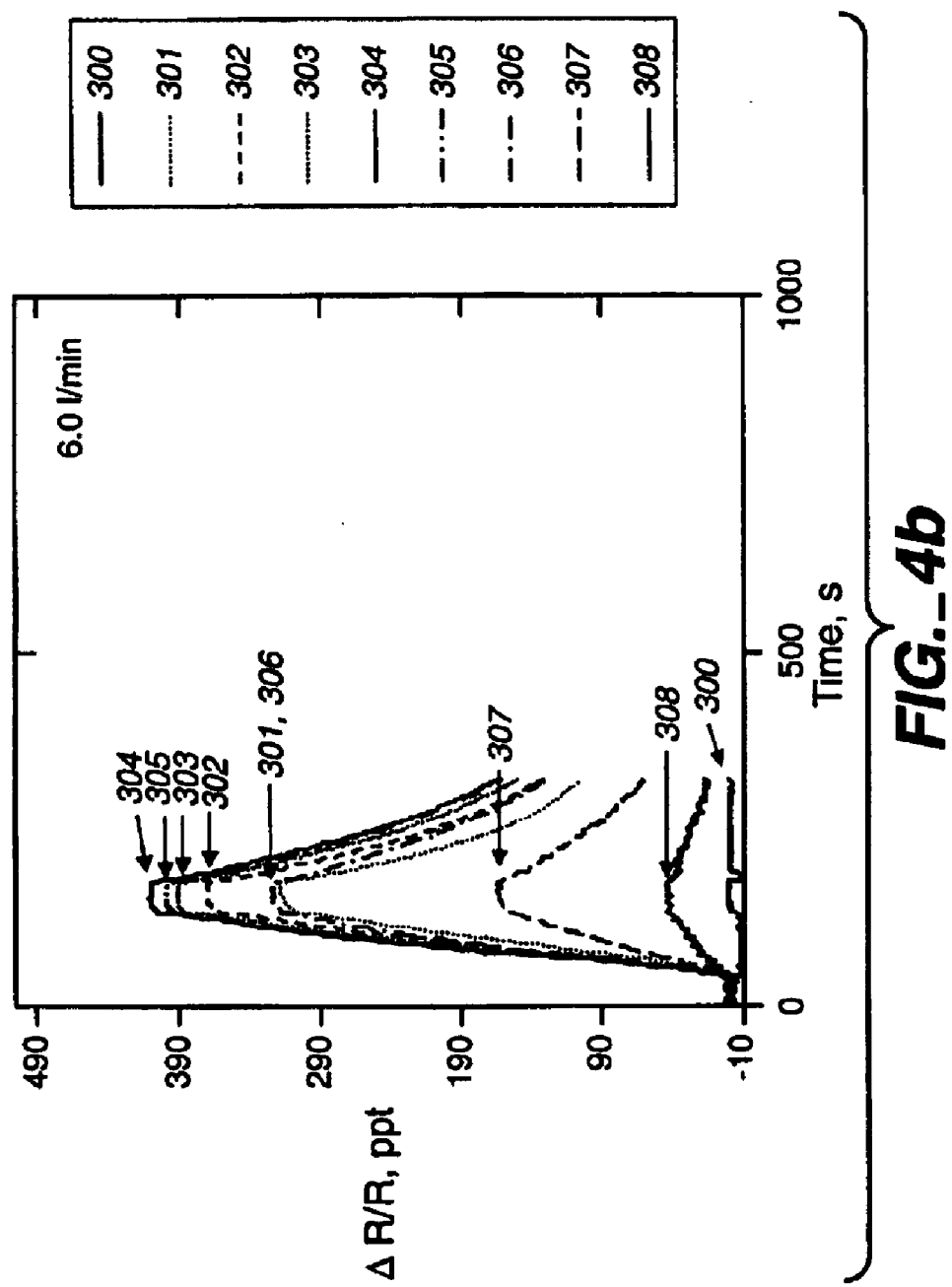
FIG._4b

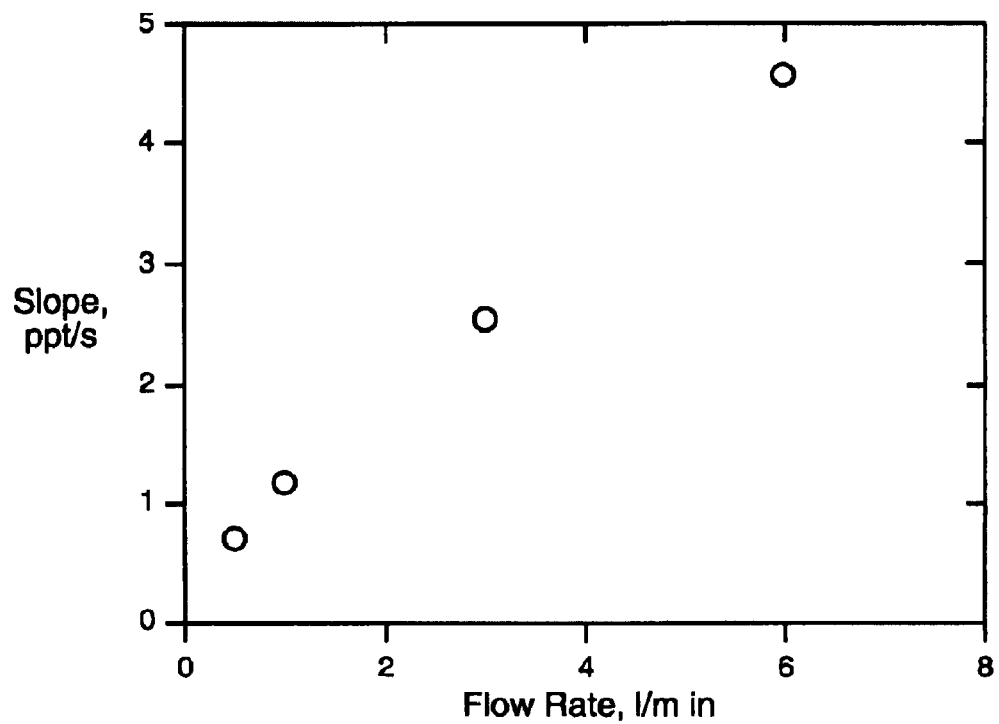
FIG._5a
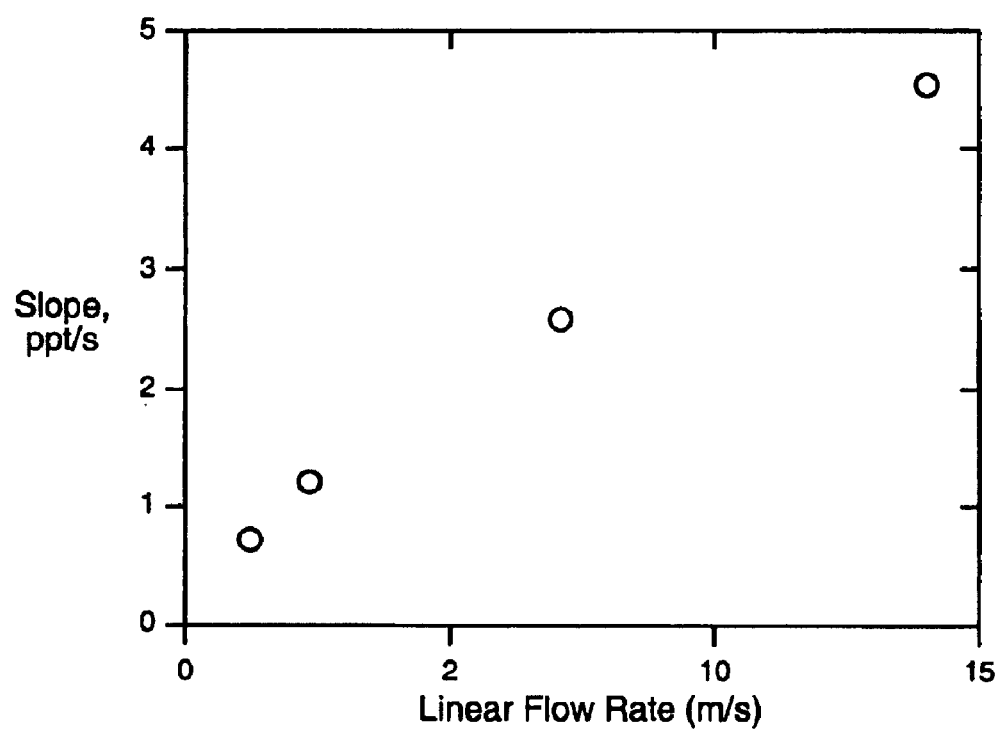
FIG._5b

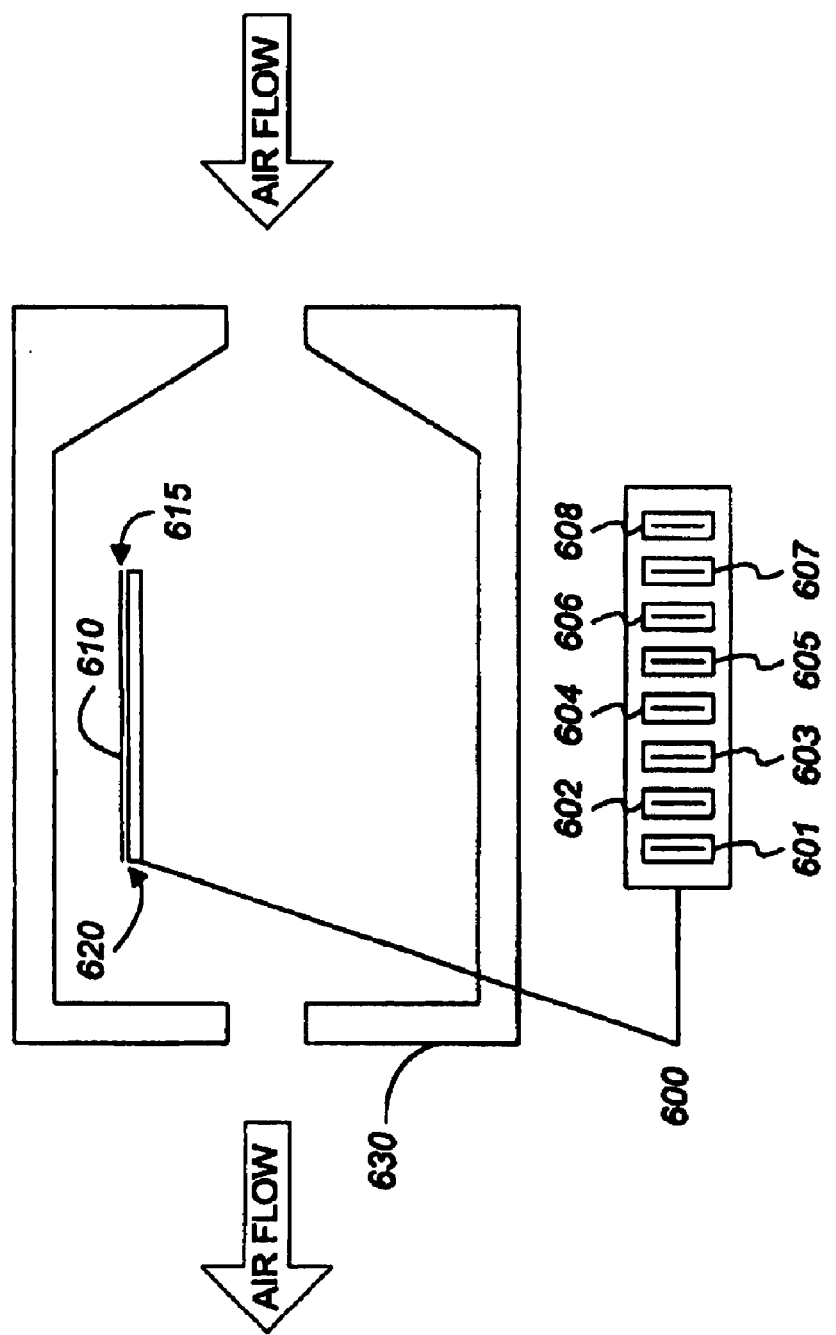
FIG._6

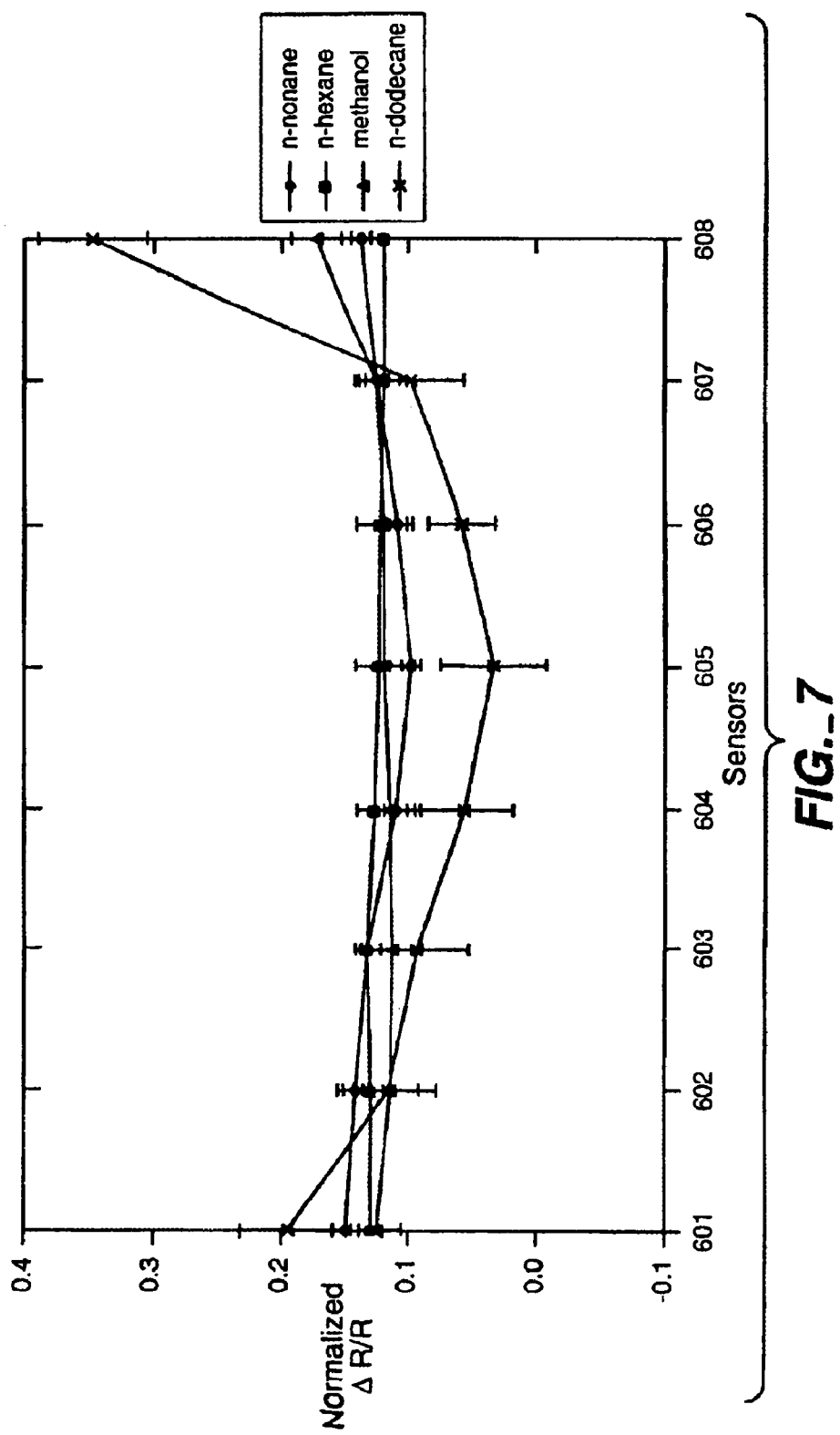
FIG._7

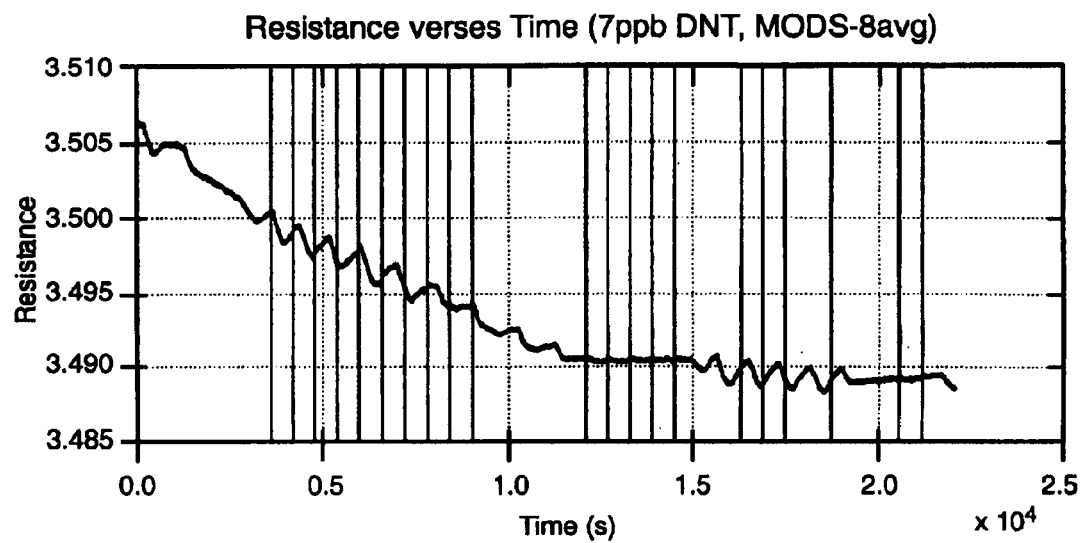
FIG._8
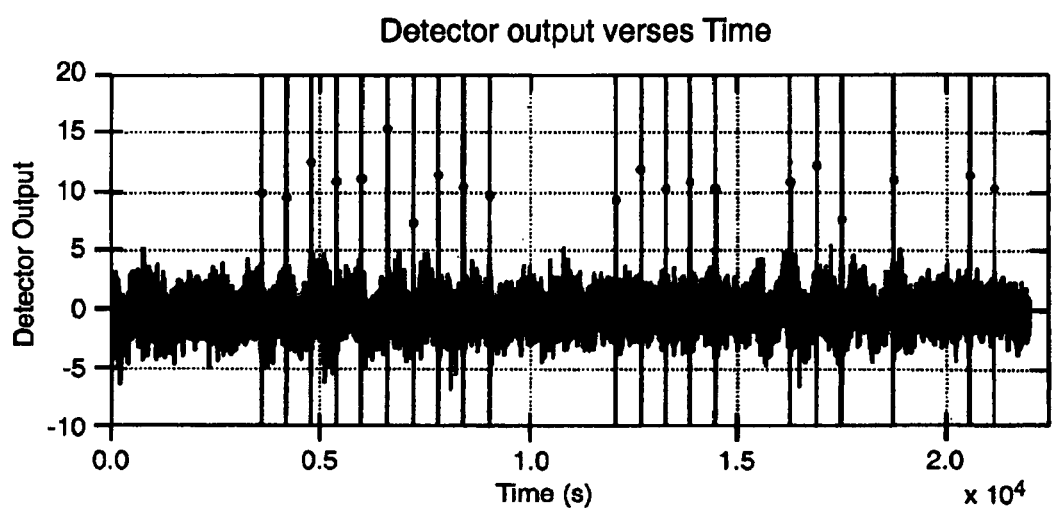
FIG._9

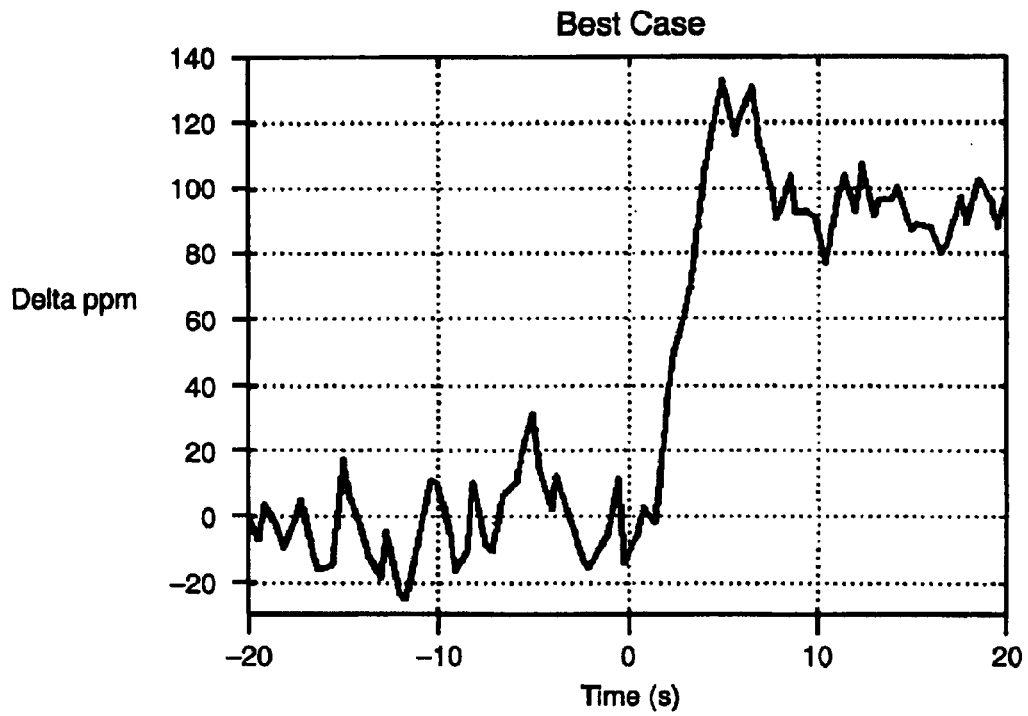
FIG._10a
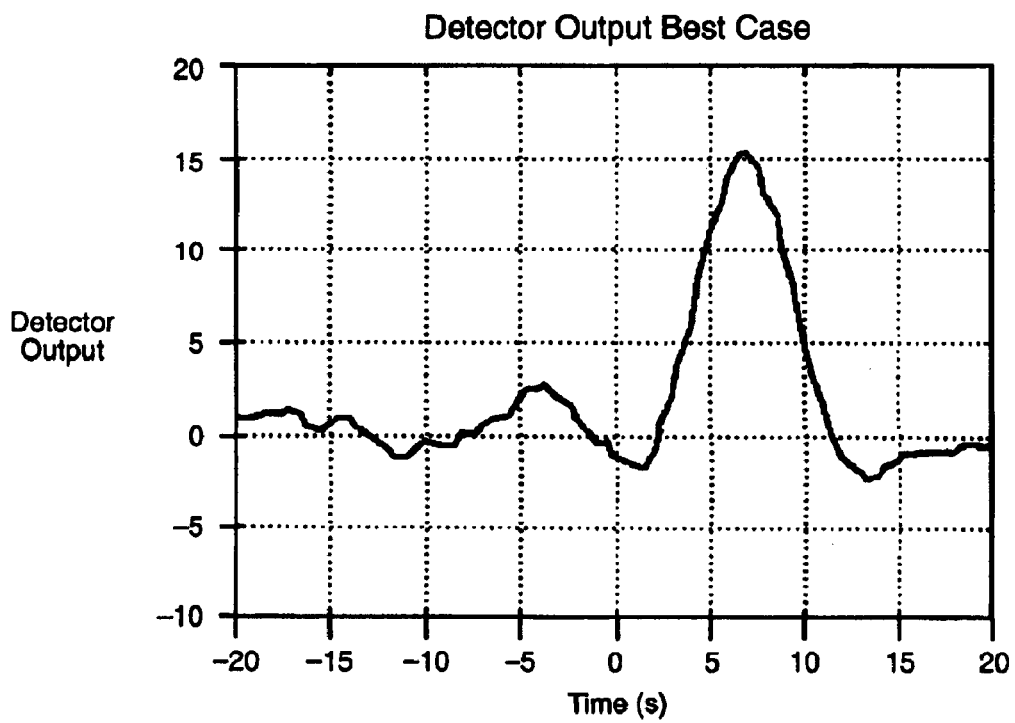
FIG._10b

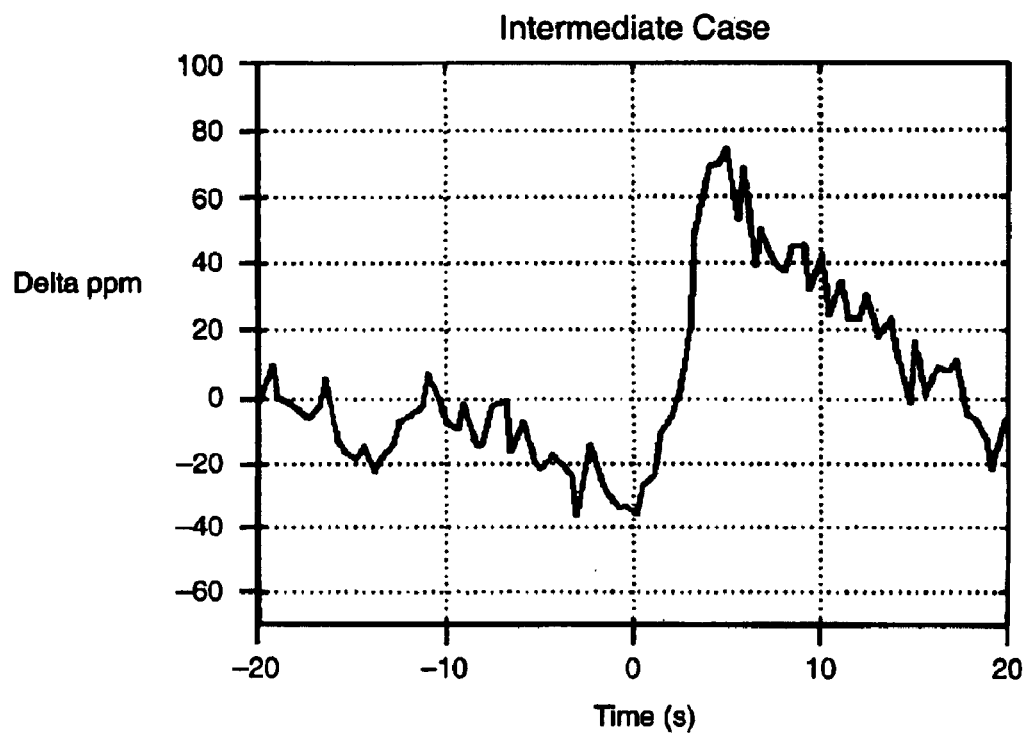
FIG._11a
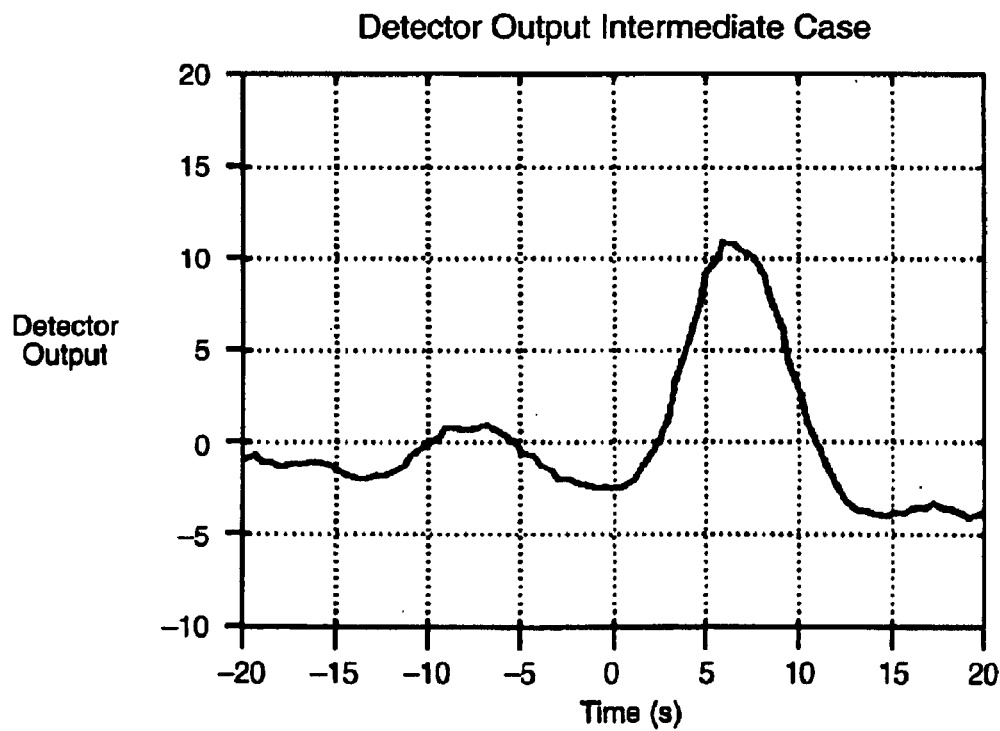
FIG._11b

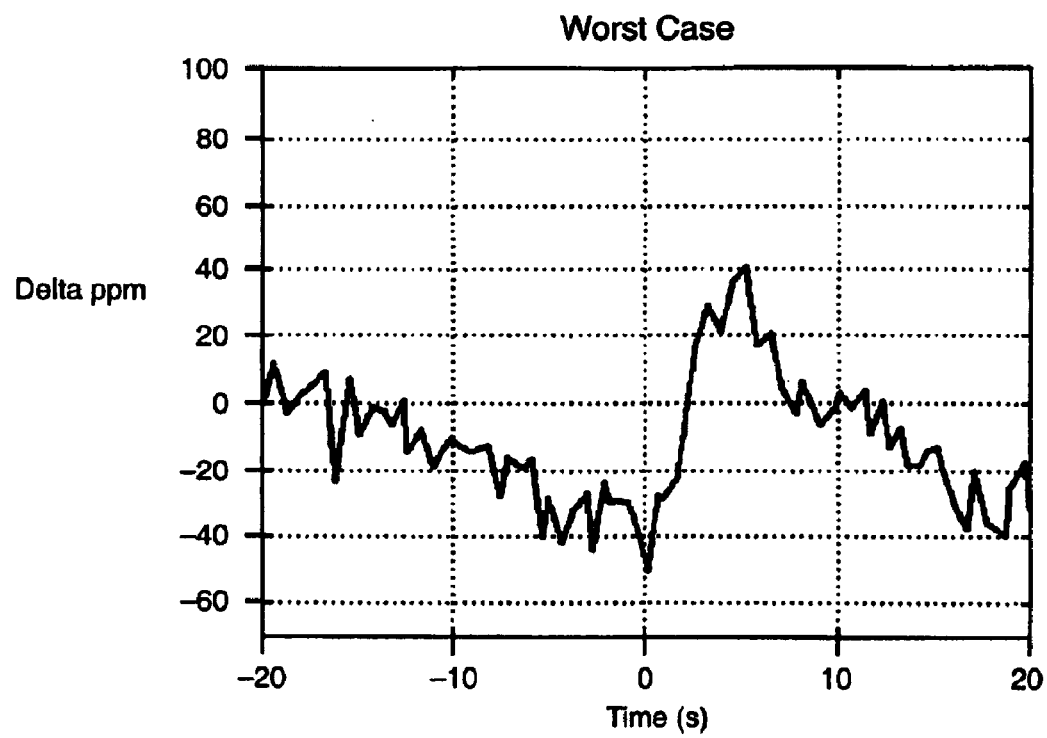
FIG._12a
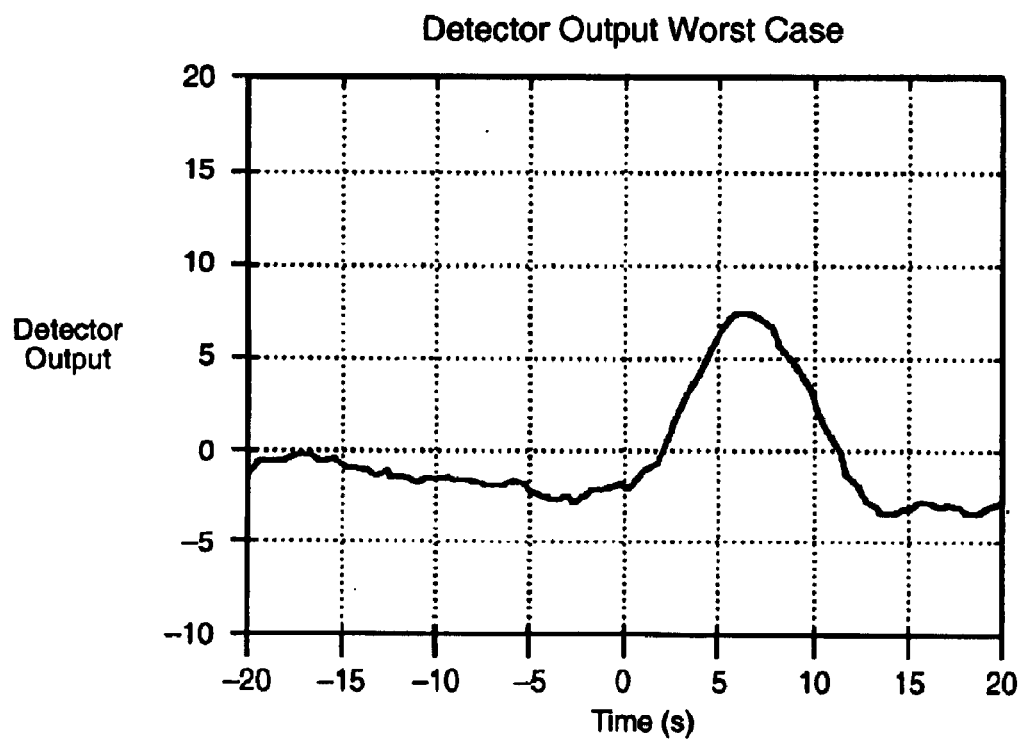
FIG._12b

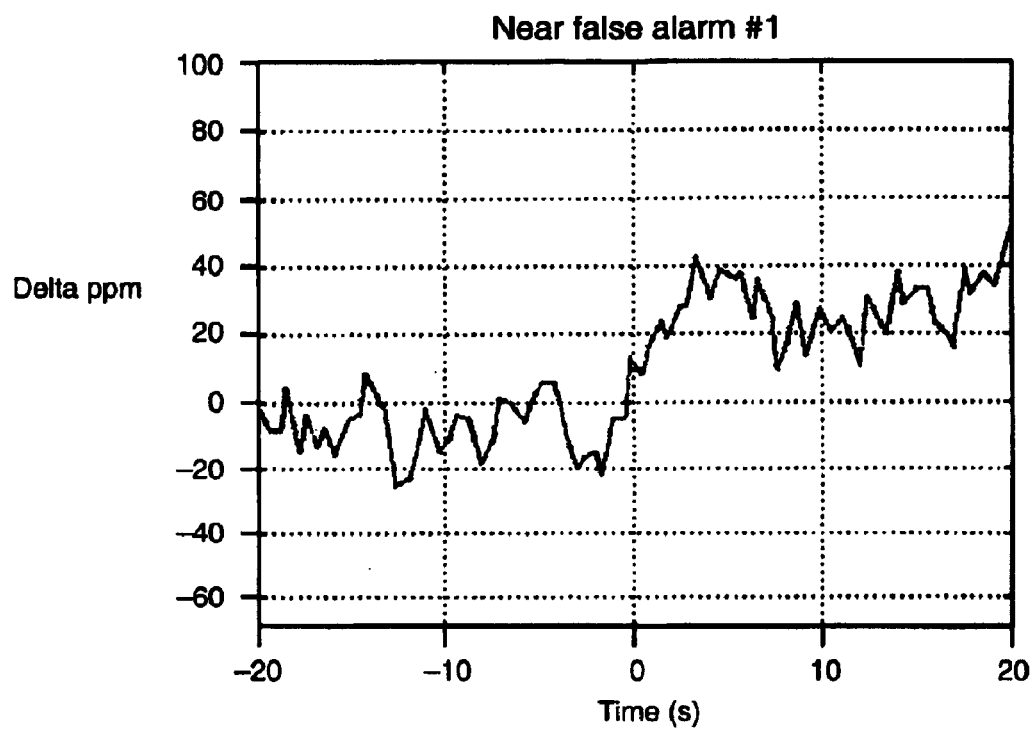
FIG._13a
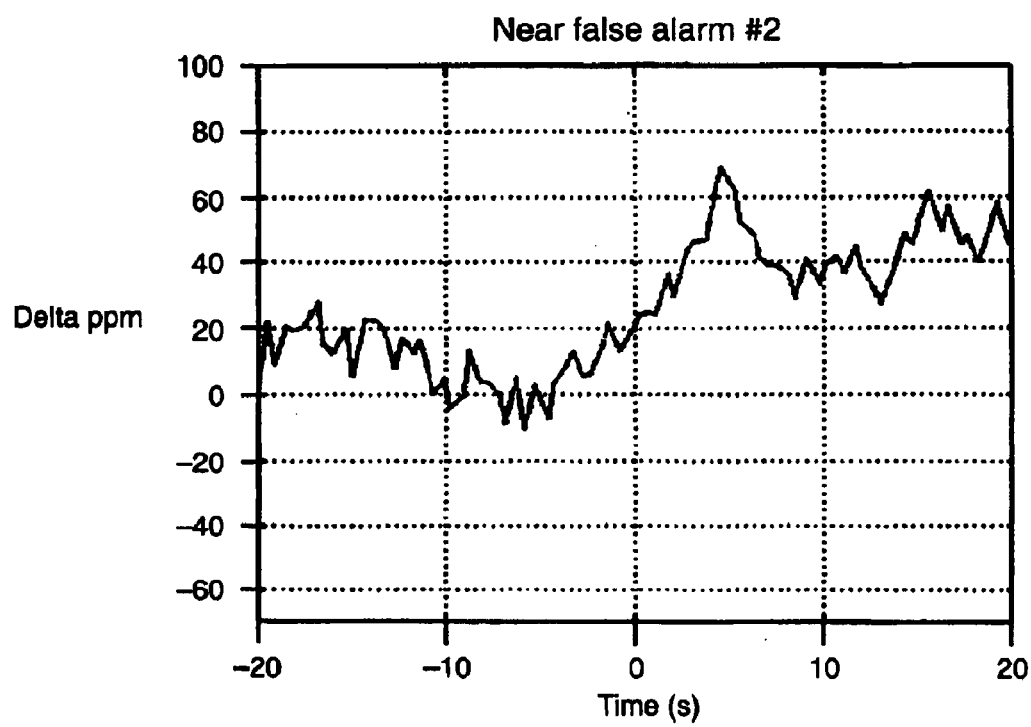
FIG._13b

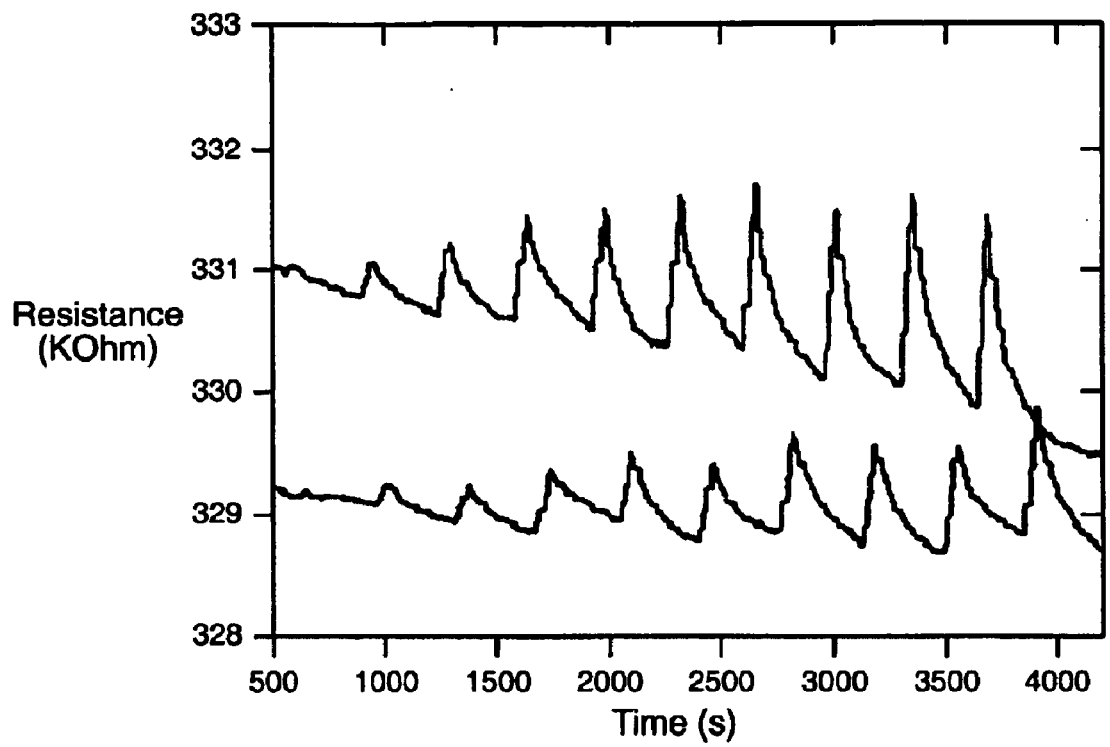
FIG._14a
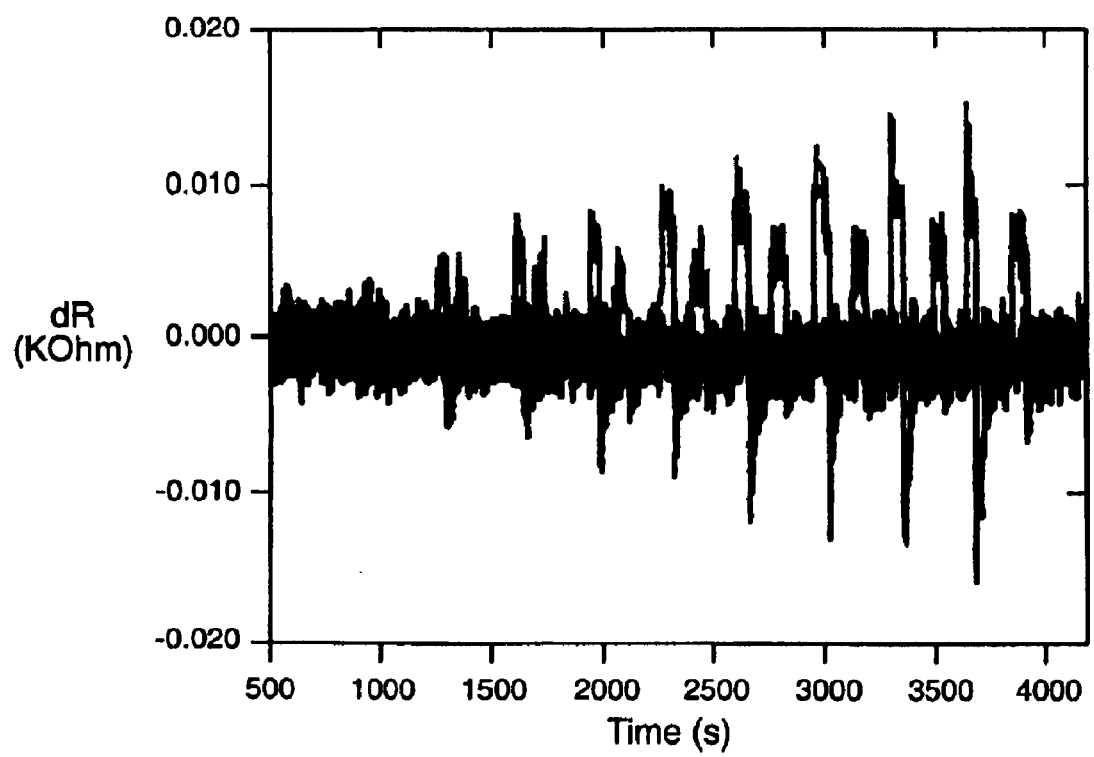
FIG._14b

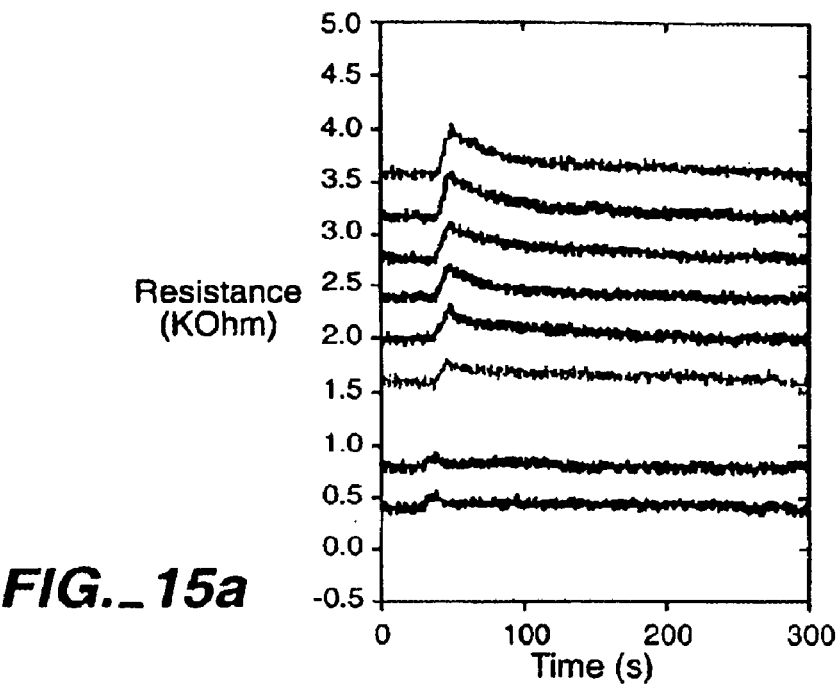
FIG._15a
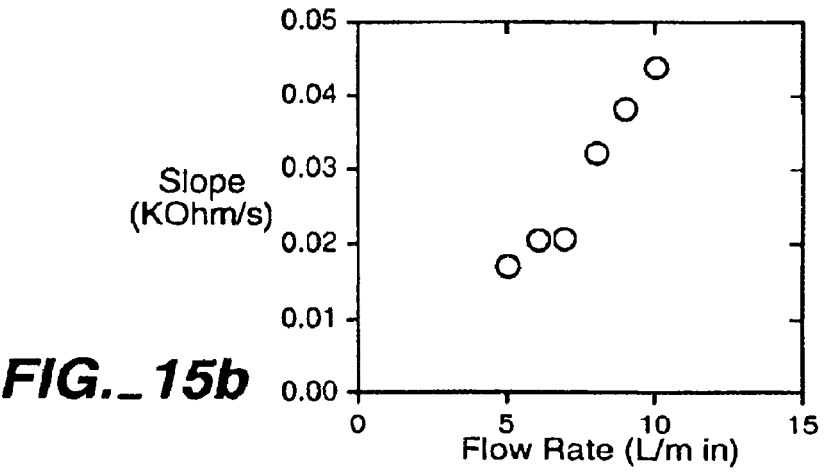
FIG._15b
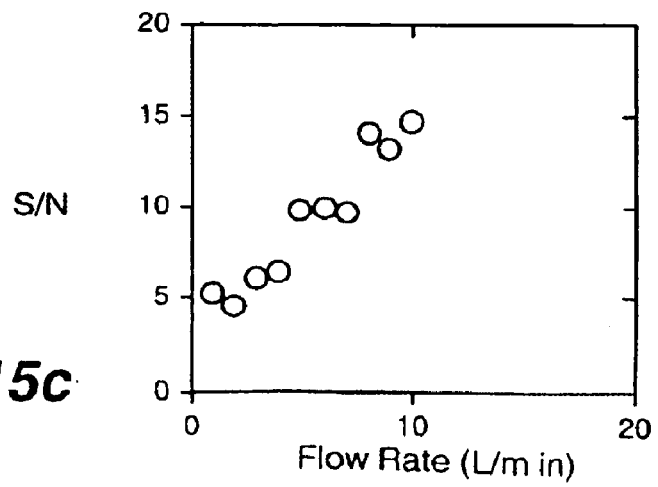
FIG._15c

USE OF SPATIOTEMPORAL RESPONSE BEHAVIOR IN SENSOR ARRAYS TO DETECT ANALYTES IN FLUIDS

CROSS REFERENCE TO RELATED APPLICATIONS

This application is a divisional of and claims priority to U.S. application Ser. No. 09/568,784, filed May 10, 2000, now U.S. Pat. No. 6,455,319, which claims the benefit of Provisional Application No. 60/133,318, filed May 10, 1999 and Provisional Application No. 60/140,027, filed Jun. 16, 1999. Each of these prior applications is incorporated by reference herein.

STATEMENT REGARDING FEDERALLY SPONSORED RESEARCH

The U.S. Government has certain rights in this invention pursuant to Contract No. DAAK60-97-K-9503 administered by the Defense Advanced Research Projects Agency and Grant No. DAAG55-97-1-0187.

BACKGROUND

The invention relates to sensors and sensor systems for detecting analytes in fluids.

There is considerable interest in developing sensors that act as analogs of the mammalian olfactory system (Lundstrom et al. (1991) Nature 352:47–50; Shurmer and Gardner (1992) Sens. Act. B 8:1–11; Shurmer and Gardner (1993) Sens. Act. B 15:32). In practice, most chemical sensors suffer from some interference by responding to chemical species that are structurally or chemically similar to the desired analyte. This interference is an inevitable consequence of the "lock" being able to fit a number of imperfect "keys". Such interferences limit the utility of such sensors to very specific situations.

Arrays of broadly cross-reactive sensors have been exploited to produce response patterns that can be used to fingerprint, classify, and in some cases quantify analytes in fluids. Such arrays have been produced incorporating sensors including heated metal oxide thin film resistors (Gardner et al. (1991) Sens. Act. B4:117–121; Gardner et al. (1992) Sens. Act. B 6:71–75), polymer sorption layers on the surfaces of acoustic wave resonators(Grate and Abraham (1991) Sens. Act. B 3:85–111; Grate et al. (1993) Anal. Chem. 65:1868–1881), arrays of electrochemical sensors (Stetter et al. (1986) Anal. Chem. 58:860–866; Stetter et al. (1990) Sens. Act. B 1:43–47; Stetter et al. (1993) Anal. Chem. Acta 284:1–11), conductive polymers or composites that consist of regions of conductors and regions of insulating organic materials (Pearce et al. (1993) Analyst 118:371–377; Shurmer et al. (1991) Sens. Act. B 4:29–33; Doleman et al. (1998) Anal. Chem. 70:2560–2654; Lonergan et al. Chem. Mater. 1996, 8:2298). Arrays of metal oxide thin film resistors, typically based on tin oxide ($SnO_2$) films that have been coated with various catalysts, yield distinct, diagnostic responses for several vapors (Corcoran et al. (1993) Sens. Act. B 15:32–37). Surface acoustic wave resonators are extremely sensitive to both mass and acoustic impedance changes of the coatings in array elements. Attempts have also been made to construct arrays of sensors with conducting organic polymer elements that have been grown electrochemically through use of nominally identical polymer films and coatings. Moreover, Pearce et al., (1993) Analyst 118:371–377, and Gardner et al., (1994) Sensors and Actuators B 18–19:240–243 describe polypyrrole based sensor arrays for monitoring beer flavor. Shurmer (1990) U.S. Pat. No. 4,907,441, describes general sensor arrays with particular electrical circuitry. U.S. Pat. No. 4,674,320 describes a single chemoresistive sensor having a semiconductive material selected from the group consisting of phthalocyanine, halogenated phthalocyanine and sulfonated phthalocyanine, which was used to detect a gas contaminant. Other gas sensors have been described by Dogan et al., Synth. Met. 60, 27–30 (1993) and Kukla, et al. Films. Sens. Act. B., Chemical 37, 135–140 (1996).

Sensor arrays formed from a plurality of composites that consist of regions of a conductor and regions of an insulating organic material, usually an organic polymer as described in U.S. Pat. No. 5,571,401, have sensitivities that are primarily dictated by the swelling-induced sorption of a vapor into the composite material, and analytes that sorb to similar extents produce similar swellings and therefore produce similar detected signals (Doleman, et al., (1998) Proc. Natl. Acad. Sci. U.S.A, 95, 5442–5447).

In these systems, the different responses from an analyte exposure to the array of sensors is used to identify the analyte. Other properties of the devices are designed to insure that otherwise all sensors are nominally equivalent so that the fluid containing the analyte is delivered to all sensors equally effectively—for example, at the same temperature— so that only the differences in sensors' response properties are being measured.

Although these sensor systems have some usefulness, there remains a need in the art for highly-selective sensor arrays for detecting analytes and resolving the components of complex mixtures.

SUMMARY OF THE INVENTION

The present artificial olfactory systems (or electronic noses) use arrays of many receptors to recognize an odorant. In such a configuration, the burden of recognition is not on highly specific receptors, as in the traditional "lock-and-key" molecular recognition approach to chemical sensing, but lies instead on the distributed pattern processing of the olfactory bulb and the brain. The system takes advantage of the spatio-temporal response differences between nominally identical sensors that are located at different positions in a fluid flow pattern.

In general, in one aspect, the invention provides a method of detecting an analyte in a fluid. The method includes providing a sensor array including at least a first sensor and a second sensor in an arrangement having a defined fluid flow path; exposing the sensor array to a fluid including an analyte by introducing the fluid along the fluid flow path; measuring a response for the first sensor and the second sensor; and detecting the presence of the analyte in the fluid based on a spatio-temporal difference between the responses for the first and second sensors.

Particular implementations of the invention can include one or more of the following features. Detecting the presence of the analyte can include generating a spatio-temporal response profile indicative of the presence of the analyte based on the spatio-temporal difference between the responses for the first and second sensors. The spatio-temporal response profile can be derived from time information indicating the dependence of sensor response on time. The first sensor can be exposed to the fluid before the second sensor, such that the response of the second sensor is delayed with respect to the response of the first sensor. The first sensor can be exposed to the fluid before the second sensor, such that the response of the second sensor is changed in amplitude with respect to the response of the first sensor. The first sensor can include a sensing material; and the response of the first sensor can be greater than the response of the second sensor for an analyte having a high affinity for the sensing material. The first and second sensors can be selected and arranged to provide a first delay between the response of the first sensor and the response of the second sensor upon exposure of the sensor array to a fluid including a first analyte and a second delay between the response of the first sensor and the response of the second sensor upon exposure of the sensor array to a fluid including a second analyte. Measuring the response can include measuring the delay between the response of the first sensor and the response of the second sensor, and the spatio-temporal difference between the responses for the first and second sensors can be derived from the delay. The method can include characterizing the analyte based on the spatio-temporal difference between the responses. Exposing the sensor array to the fluid can include introducing the fluid at a varying flow rate. Generating the spatio-temporal response profile can include generating flow information indicating the dependence of sensor response on flow rate. The sensor array can include a plurality of cross-reactive sensors. The sensor array can include a plurality of sensors selected from the group including surface acoustic wave sensors, quartz crystal resonators, metal oxide sensors, dye-coated fiber optic sensors, dye-impregnated bead arrays, micromachined cantilever arrays, composites having regions of conducting material and regions of insulating organic material, composites having regions of conducting material and regions of conducting or semiconducting organic material, chemically-sensitive resistor or capacitor films, metal-oxide-semiconductor field effect transistors, and bulk organic conducting polymeric sensors. The first and second sensors can include composites having regions of a conducting material and regions of an insulating organic material. The first and second sensors can include composites having regions of a conducting material and regions of a conducting organic material. The method can include generating a digital representation of the analyte based at least in part on the responses of the first and second sensors. The method can include communicating the digital representation of the analyte to a remote location for analysis.

In general, in another aspect, the invention provides a system for detecting an analyte in a fluid. The system includes a sensor array including at least a first sensor and a second sensor in an arrangement having a defined fluid flow path; a measuring apparatus coupled to the sensor array, the measuring apparatus being configured to detect a response from the first sensor and the second sensor upon exposure of the sensor array to a fluid; and a computer configured to generate data indicating the presence of the analyte in the fluid based on a spatio-temporal difference between the responses for the first and second sensors.

Particular implementations of the invention can include one or more of the following features. The data indicating the presence of the analyte in the fluid can include a spatio-temporal response profile derived from the spatio-temporal difference between the responses for the first and second sensors. The spatio-temporal response profile is derived from time information indicating the dependence of sensor response on time. The first sensor can occupy a first position in the arrangement and the second sensor a second position in the arrangement, such that the response of the second sensor is delayed in time with respect to the response of the first sensor upon exposure of the sensor array to the fluid. The first sensor can occupy a first position in the arrangement and the second sensor a second position in the arrangement, such that the response of the second sensor is changed in amplitude with respect to the response of the first sensor upon exposure of the sensor array to the fluid. The first sensor can include a sensing material, and the response of the first sensor can be greater than the response of the second sensor for an analyte having a high affinity for the sensing material. The first and second sensors can be selected and arranged to provide a first delay between the response of the first sensor and the response of the second sensor upon exposure of the sensor array to a fluid including a first analyte and a second delay between the response of the first sensor and the response of the second sensor upon exposure of the sensor array to a fluid including a second analyte. The measuring apparatus can be configured to measure the delay between the response of the first sensor and the response of the second sensor; and the spatio-temporal difference between the responses for the first and second sensors can be derived from the delay. The computer can be configured to characterize the analyte based on the spatio-temporal difference between the responses. The system can include a flow controller to introduce the fluid to the sensor array at a varying flow rate. The computer can be configured to generate flow information indicating the dependence of sensor response on flow rate. The sensor array can include a plurality of cross-reactive sensors. The sensor array can include a plurality of sensors selected from the group including surface acoustic wave sensors, quartz crystal resonators, metal oxide sensors, dye-coated fiber optic sensors, dye-impregnated bead arrays, micromachined cantilever arrays, composites having regions of conducting material and regions of insulating organic material, composites having regions of conducting material and regions of conducting or semiconducting organic material, chemically-sensitive resistor or capacitor films, metal-oxide-semiconductor field effect transistors, and bulk organic conducting polymeric sensors. The first and second sensors can include composites having regions of a conducting material and regions of an insulating organic material. The first and second sensors can include composites having regions of a conducting material and regions of a conducting organic material. The computer can be configured to generate a digital representation of the analyte based at least in part on the responses of the first and second sensors. The system can include a communications port coupled to the computer for communicating the digital representation of the analyte to a remote location for analysis.

In general, in still another aspect, the invention provides a system for detecting an analyte in a fluid. The system includes a sensor array including a first sensor and a second sensor, a fluid inlet proximate to the sensor array, and a measuring apparatus connected to the sensor array. The fluid inlet defines a fluid flow pattern for the introduction of a fluid onto the sensor array, such that the first and second sensors are located at different locations in the sensor array relative to the fluid flow pattern. The measuring apparatus is configured to detect a response from the first sensor and the second sensor upon exposure of the sensor array to a fluid. The responses define a spatio-temporal difference between the responses for the first and second sensors based on the locations of the sensors relative to the fluid flow pattern.

Particular implementations of the invention can include one or more of the following features. The spatio-temporal difference can be derived from time information indicating the dependence of sensor response on time. The first sensor can occupy a first position relative to the fluid flow pattern and the second sensor a second position relative to the fluid flow pattern, such that the response of the second sensor is delayed with respect to the response of the first sensor upon exposure of the sensor array to the fluid. The first sensor can occupy a first position relative to the fluid flow pattern and the second sensor a second position relative to the fluid flow pattern, such that the response of the second sensor is changed in amplitude with respect to the response of the first sensor upon exposure of the sensor array to the fluid. The first sensor can include a sensing material and the response of the first sensor can be greater than the response of the second sensor for an analyte having a high affinity for the sensing material. The first and second sensors can be selected and arranged to provide a first delay between the response of the first sensor and the response of the second sensor upon exposure of the sensor array to a fluid including a first analyte and a second delay between the response of the first sensor and the response of the second sensor upon exposure of the sensor array to a fluid including a second analyte. The measuring apparatus can be configured to measure the delay between the response of the first sensor and the response of the second sensor, and the spatio-temporal difference between the responses for the first and second sensors can be derived from the delay. The system can include a computer configured to characterize the analyte based on the spatio-temporal difference between the responses. The system can include a flow controller to introduce the fluid to the sensor array at a varying flow rate. The measuring apparatus can be configured to measure flow information indicating the dependence of sensor response on flow rate. The sensor array can include a plurality of cross-reactive sensors. The system sensor array can include a plurality of sensors selected from the group including surface acoustic wave sensors, quartz crystal resonators, metal oxide sensors, dye-coated fiber optic sensors, dye-impregnated bead arrays, micromachined cantilever arrays, composites having regions of conducting material and regions of insulating organic material, composites having regions of conducting material and regions of conducting or semiconducting organic material, chemically-sensitive resistor or capacitor films, metal-oxide-semiconductor field effect transistors, and bulk organic conducting polymeric sensors. The first and second sensors can include composites having regions of a conducting material and regions of an insulating organic material. The first and second sensors can include composites having regions of a conducting material and regions of a conducting organic material. The computer can be configured to generate a digital representation of the analyte based at least in part on the responses of the first and second sensors.

In general, in still another aspect, the invention provides a system for detecting an analyte in a fluid. The system includes a sensor array including a first sensor and a second sensor; a fluid flow exposing the first and second sensors to a fluid, such that the first and second sensors occupy different locations in the sensor array relative to the fluid flow; and a measuring apparatus connected to the sensor array. The measuring apparatus is configured to detect a response from the first and second sensors upon exposure of the sensor array to the fluid flow. The responses define a spatio-temporal difference based on the locations of the sensors in the sensor array relative to the fluid flow.

Particular implementations of the invention can include one or more of the following features. The spatio-temporal difference can be derived from time information indicating the dependence of sensor response on time. The first sensor can occupy a first position relative to the fluid flow and the second sensor a second position relative to the fluid flow, such that the response of the second sensor is delayed with respect to the response of the first sensor upon exposure of the sensor array to the fluid. The first sensor can occupy a first position relative to the fluid flow and the second sensor occupies a second position relative to the fluid flow, such that the response of the second sensor is changed in amplitude with respect to the response of the first sensor upon exposure of the sensor array to the fluid. The first sensor can include a sensing material, and the response of the first sensor can be greater than the response of the second sensor for an analyte having a high affinity for the sensing material. The first and second sensors can be selected and arranged to provide a first delay between the response of the first sensor and the response of the second sensor upon exposure of the sensor array to a fluid including a first analyte and a second delay between the response of the first sensor and the response of the second sensor upon exposure of the sensor array to a fluid including a second analyte. The measuring apparatus can be configured to measure the delay between the response of the first sensor and the response of the second sensor, and the spatio-temporal difference between the responses for the first and second sensors can be derived from the delay. The system can include a computer configured to characterize the analyte based on the spatio-temporal difference between the responses. The system can include a flow controller to vary the rate of the fluid flow. The measuring apparatus can be configured to measure flow information indicating the dependence of sensor response on flow rate. The sensor array can include a plurality of cross-reactive sensors. The sensor array can include a plurality of sensors selected from the group including surface acoustic wave sensors, quartz crystal resonators, metal oxide sensors, dye-coated fiber optic sensors, dye-impregnated bead arrays, micromachined cantilever arrays, composites having regions of conducting material and regions of insulating organic material, composites having regions of conducting material and regions of conducting or semiconducting organic material, chemically-sensitive resistor or capacitor films, metal-oxide-semiconductor field effect transistors, and bulk organic conducting polymeric sensors. The first and second sensors can include composites having regions of a conducting material and regions of an insulating organic material. The first and second sensors can include composites having regions of a conducting material and regions of a conducting organic material. The computer can be configured to generate a digital representation of the analyte based at least in part on the responses of the first and second sensors.

In general, in still another aspect, the invention provides a sensor array for detecting an analyte in a fluid. The sensor array includes a substrate; a first sensor coupled to the substrate at a first location; and a second sensor coupled to the substrate at a second location, such that the first and second sensors occupy different locations in the sensor array relative to a fluid flow path.

Particular implementations of the invention can include one or more of the following features. The first sensor can occupy a first position relative to the fluid flow path and the second sensor a second position relative to the fluid flow path, the first sensor being configured to provide a first response upon exposure of the sensor array to a fluid and the second sensor being configured to provide a second response upon exposure of the sensor array to the fluid, such that the second response is delayed with respect to the first response upon exposure of the sensor array to the fluid. The first sensor can provide a first time-dependent response upon exposure of the sensor array to a fluid, and the second sensor can provide a second time-dependent response upon exposure of the sensor array to the fluid. The first sensor can occupy a first position relative to the fluid flow path and the second sensor a second position relative to the fluid flow path, such that the second time-dependent response is changed in amplitude with respect to the first time-dependent response upon exposure of the sensor array to the fluid. The first sensor can include a sensing material, and the response of the first sensor can be greater than the response of the second sensor for an analyte having a high affinity for the sensing material. The first and second sensors can be selected and arranged to provide a first delay between a response of the first sensor and a response of the second sensor upon exposure of the sensor array to a fluid including a first analyte and a second delay between a response of the first sensor and a response of the second sensor upon exposure of the sensor array to a fluid including a second analyte. The sensor array can include a plurality of cross-reactive sensors. The sensor array can include a plurality of sensors selected from the group including surface acoustic wave sensors, quartz crystal resonators, metal oxide sensors, dye-coated fiber optic sensors, dye-impregnated bead arrays, micromachined cantilever arrays, composites having regions of conducting material and regions of insulating organic material, composites having regions of conducting material and regions of conducting or semiconducting organic material, chemically-sensitive resistor or capacitor films, metal-oxide-semiconductor field effect transistors, and bulk organic conducting polymeric sensors. The first and second sensors can include composites having regions of a conducting material and regions of an insulating organic material. The first and second sensors can include composites having regions of a conducting material and regions of a conducting organic material.

Advantages that can be seen in implementations of the invention include one or more of the following. Taking advantage of a spatio-temporal property of a sensor array can impart very useful information on analyte identification and detection relative to arrays where no spatiotemporal information is available because all sensors are nominally in identical positions with respect to the fluid flow characteristics and are exposed to the analyte at nominally identical times during the fluid sampling experiment. Electronics can be implemented to record the time delay between sensor responses and to use this information to characterize the analyte of interest in the fluid. This mode can also be advantageous because it can allow automatic nulling of any sensor drift, environmental variations (such as temperature, humidity, etc.) and the like. Also, a complex odor mixture can be better resolved into its components based on the spatiotemporal characteristics of the array response relative only to the differences in fingerprints on the various sensors types in the array. Additionally, these techniques can be used in conjunction with differential types of measurements to selectively detect only certain classes or types of analytes, because the detection can be gated to only focus on signals that exhibit a desired correlation time between their responses on the sensors that are in different exposure times relative to the sensor response on the first sensor that detects an analyte.

BRIEF DESCRIPTION OF THE FIGURES

These and other objects of the present invention will now be described in detail with reference to the accompanying drawings, in which:

FIG. 1 is a block diagram illustrating a system for detecting an analyte in a fluid.

FIG. 2 is a flow diagram illustrating a method of detecting an analyte in a fluid.

FIG. 3 illustrates one implementation of a system for detecting an analyte in a fluid according to the invention.

FIGS. 4a–b are plots of sensor response as a function of time for the sensor array shown in FIG. 3.

FIGS. 5a–b are plots of response as a function of flow rate and linear flow rate, respectively, for one sensor in the array shown in FIG. 3.

FIG. 6 is a schematic diagram illustrating an alternate implementation of a system for detecting an analyte in a fluid according to the invention.

FIG. 7 is a graph illustrating sensor response as a function of sensor position in an experiment involving the array shown in FIG. 6.

FIG. 8 is a graph illustrating a resistance versus time profile calculated for a sensor array comprising eight nominally identical poly(methyloctadecylsiloxane)-carbon black composite sensors.

FIG. 9 is a graph illustrating a plot of sensor output versus time for the sensor array of FIG. 8.

FIGS. 10a–b are graphs illustrating the resistance (delta ppm) behavior and sensor output as a function of time for a single exposure having the largest sensor output for the experiment of FIGS. 8 and 9.

FIGS. 11a–b are graphs illustrating the resistance (delta ppm) behavior and sensor output as a function of time for a single exposure having an intermediate sensor output for the experiment of FIGS. 8 and 9.

FIGS. 12a–b are graphs illustrating the resistance (delta ppm) behavior and sensor output as a function of time for a single exposure having the smallest sensor output for the experiment of FIGS. 8 and 9.

FIGS. 13a–b are graphs illustrating the resistance (delta ppm) behavior and sensor output as a function of time for two "near miss" background windows for the experiment of FIGS. 8 and 9.

FIGS. 14a–b are graphs illustrating resistance transients and change in resistance as a function of time showing the dependence of signal from a ventilated sensor array on flow rate.

FIGS. 15a–c are graphs illustrating response transients at varying flow rates; response slope as a function of flow rate through the sensor; and signal to noise after 5 s exposure as a function of flow rate, respectively, for an experiment involving the ventilated sensor array of FIGS. 14a–b.

DETAILED DESCRIPTION OF THE INVENTION

FIG. 1 illustrates a system 100 for detecting an analyte in a fluid. System 100 includes a sensor array 110, in which an arrangement of a plurality of sensors 120 defines a fluid channel 130. Optionally, sensor array 110 is configured to include one or more fluid channels 140 in addition to fluid channel 130, each fluid channel 140 including an additional plurality of sensors 150. A fluid to be analyzed, which may be in gaseous or liquid form, is exposed to sensor array 110 through fluid inlet 160, for example from fluid reservoir 170. Response signals from the sensors 120, 150 in sensor array 110 resulting from exposure of the fluid to the sensor array are received and processed in detector 180, which may include, for example, signal-processing electronics, a general-purpose programmable digital computer system of conventional construction, or the like.

A method 200 of using system 100 to detect the presence of an analyte in a fluid is illustrated in FIG. 2. A fluid including an analyte is introduced onto a sensor array 110 (step 210). According to a flow pattern defined by the configuration of array 110 or by the introduction of the fluid, at a time t the fluid interacts with a first sensor or sensors (step 220). Detector 180 detects and records response signals from the first sensor(s) (step 230). The fluid then interacts with a second sensor or sensors at a time t+δ (step 240), and detector 180 detects and records response signals from the second sensor(s) (step 250). Steps 230 and 240 are repeated as the fluid travels across array 110, until each sensor in the array has been exposed to the fluid and the corresponding response signal recorded by detector 180 (The NO branch of step 260). The recorded response signals are then processed to detect and or characterize an analyte or combination of analytes in the fluid (step 270).

Sensors 120, 180 can include any of a variety of known sensors, including, for example, surface acoustic wave sensors, quartz crystal resonators, metal oxide sensors, dye-coated fiber optic sensors, dye-impregnated bead arrays, micromachined cantilever arrays, composites having regions of conducting material and regions of insulating organic material, composites having regions of conducting material and regions of conducting or semiconducting organic material, chemically-sensitive resistor or capacitor films, metal-oxide-semiconductor field effect transistors, bulk organic conducting polymeric sensors, and other known sensor types. Techniques for constructing arrays of such sensors are known, as disclosed in Harsanyi, G., Polymer Films in Sensor Applications (Technomic Publishing Co., Basel, Switzerland, 1995), and U.S. Pat. Nos. 6,017,440, 6,013,229 and 5,911,872 and co-pending U.S. patent application Ser. No. 09/409,644, filed Oct. 1, 1999, which are incorporated by reference herein. Techniques for fabricating particular sensor types are disclosed in Ballantine, D. S.; Rose, S. L.; Grate, J. W.; Wohltjen, H. *Anal. Chem.* 1986, 58, 3058; Grate, J. W.; Abraham, M. H. *Sens. Actuators B* 1991, 3, 85; Grate, J. W.; Rosepehrsson, S. L.; Venezky, D. L.; Klusty, M.; Wohltjen, H. *Anal. Chem.* 1993, 65, 1868; Nakamoto, T.; Fukuda, A.; Moriizumi, T. *Sens. Actuators B* 1993, 10, 85 (surface acoustic wave (SAW) devices), Gardner, J. W.; Shurmer, H. V.; Corcoran, P. *Sens. Actuators B* 1991, 4, 117; Gardner, J. W.; Shurmer, H. V.; Tan, T. T. *Sens. Actuators B* 1992, 6, 71; Corcoran, P.; Shurmer, H. V.; Gardner, J. W. *Sens. Actuators B* 1993, 15, 32 (tin oxide sensors), Shurmer, H. V.; Corcoran, P.; Gardner, J. W. *Sens. Actuators B* 1991, 4, 29; Pearce, T. C.; Gardner, J. W.; Friel, S.; Bartlett, P. N.; Blair, N. *Analyst* 1993, 118, 371 (conducting organic polymers), Freund, M. S.; Lewis, N. S. *Proc. Natl. Acad. Sci* 1995, 92, 2652 (materials having regions of conductors and regions of insulating organic material), White, J.; Kauer, J. S.; Dickinson, T. A.; Walt, D. R. *Anal. Chem.* 1996, 68, 2191 (dye-impregnated polymer films on fiber optic sensors), Butler, M. A.; Ricco, A. J.; Buss, R. *J. Electrochem. Soc.* 1990, 137, 1325; Hughes, R. C.; Ricco, A. J.; Butler, M. A.; Pfeifer, K. B. *J. Biochem. and Biotechnol.* 1993, 41, 77 (polymer-coated micromirrors), Slater, J. M.; Paynter, J. *Analyst* 1994, 119, 191; Slater, J. M.; Watt, E. J. *Analyst* 1991, 116, 1125 (quartz crystal microbalances (QCMs)), Keyvani, D.; Maclay, J.; Lee, S.; Stetter, J.; Cao, Z. *Sens. Actuators B* 1991, 5, 199 (electrochemical gas sensors), Zubkans, J.; Spetz, A. L.; Sundgren, H.; Winquist, F.; Kleperis, J.; Lusis, A.; Lundstrom, I. *Thin Solid Films* 1995, 268, 140 (chemically sensitive field-effect transistors) and Lonergan, M. C.; Severin, E. J.; Doleman, B. J.; Beaber, S. A.; Grubbs, R. H.; Lewis, N. S. *Chem. Mater.* 1996, 8, 2298 carbon black-polymer composite chemiresistors ). Additional sensor array fabrication techniques are disclosed in Albert, K. J., Lewis, N. S., et al., Cross-Reactive Chemical Sensor Arrays, *Chemical Reviews,* 2000, 100 (in press) and the references cited therein.

In one implementation, sensor array 110 incorporates multiple sensing modalities, for example comprising a spatial arrangement of cross-reactive sensors 120, 180 selected from known sensor types, such as those listed above, such that a given analyte elicits a response from multiple sensors in the array and each sensor responds to many analytes. Preferably, the sensors in the array 110 are broadly cross-reactive, meaning each sensor in the array responds to multiple analytes, and, in turn, each analyte elicits a response from multiple sensors.

Sensor arrays allow expanded utility because the signal for an imperfect "key" in one channel can be recognized through information gathered on another, chemically or physically dissimilar channel in the array. A distinct pattern of responses produced over the collection of sensors in the array can provide a fingerprint that allows classification and identification of the analyte, whereas such information would not have been obtainable by relying on the signals arising solely from a single sensor or sensing material. By developing an empirical catalogue of information on chemically diverse sensors—made, for example, with varying ratios of semiconductive, conducting, and insulating components and by differing fabrication routes—sensors can be chosen that are appropriate for the analytes expected in a particular application, their concentrations, and the desired response times. Further optimization can then be performed in an iterative fashion as feedback on the performance of an array under particular conditions becomes available.

The sensor arrays of system 100 provide still further benefits by incorporating spatio-temporal response information that is exploited by detector 180 to aid in analyte detection and identification. Taking advantage of a spatio-temporal property of a sensor array can impart useful information on analyte detection and identification relative to arrays where no spatiotemporal information is available because all sensors are nominally in identical positions with respect to the fluid flow characteristics and are exposed to the analyte at nominally identical times during the fluid sampling experiment. Electronics can be implemented in detector 180 to record a time delay between sensor responses and to use this information to characterize the analyte of interest in the fluid. This mode can also be advantageous because it can allow automatic nulling of any sensor drift, environmental variations (such as temperature, humidity, etc.) and the like. Also, a complex analyte mixture can be better resolved into its components based on the spatiotemporal characteristics of the array response relative only to the differences in fingerprints on the various sensors types in the array. Additionally, the method can be used in conjunction with differential types of measurements to selectively detect only certain classes or types of analytes, because the detection can be gated to only focus on signals that exhibit a desired correlation time between their responses on the sensors that are in different exposure times relative to the sensor response on the first sensor that detects an analyte.

Thus, for example, sensor arrays 110 can be configured such that low vapor pressure analytes in the gas phase will have a high affinity towards the sensors and will sorb strongly to them. This strong sorption produces a strong response at the first downstream sensor that the analyte encounters, a weaker response at the second downstream sensor, and a still weaker response at other downstream sensors. Different analytes will produce a detectable and useful time delay between the response of the first sensor and the response of the other downstream sensors. As a result, detector 180 can use the differences in response time and amplitude to detect and characterize analytes in a carrier fluid, analogous to the use of gas chromatography retention times, which are well known in the gas chromatography literature and art.

Spatio-temporal information can be obtained from an array of two or more sensors by varying the sensors' exposure to the fluid containing the analyte across the array (e.g., by generating a spatial and/or temporal gradient across the array), thereby allowing responses to be measured simultaneously at various different exposure levels and for various different sensor compositions. For example, an array 110 of sensors 120, 150, can be configured to vary the composition of the sensors in the horizontal direction across the array, such that sensor composition in the vertical direction across the array remains constant. One may then create a spatio-temporal gradient in the vertical direction across the array— for example, by introducing the fluid from the top of the array and providing for fluid flow vertically down the array, thereby allowing the simultaneous analysis of chemical analytes at different sensor compositions and different exposure levels. Similarly, in an array 110 including a plurality of different sensors 120, 150 (i.e., an array in which each sensor is of a different type or composition), spatio-temporal variation can be introduced by systematically varying the flow rate at which the analyte-containing fluid is exposed to the sensors in the array. Again, in this implementation, measuring the response of each of the sensors 120, 150 at a variety of different flow rates allows the simultaneous analysis of analytes at different sensor compositions and different exposure levels.

Thus, in one implementation, the sensors 120, 150 defining each fluid channel 130, 140 are nominally identical— that is, the sensors 120, 150 within a given fluid channel 130, 140 are identical. In contrast, sensor array 110 incorporates a predetermined inter-sensor variation in the chemistry, structure or composition of the sensors 120, 150 between fluid channels 130, 140. The variation may be quantitative and/or qualitative. For example, different channels 130, 140 can be constructed to incorporate sensors of different types, such as incorporating a plurality of nominally identical metal oxide gas sensors in a fluid channel 130, a plurality of conducting polymer sensors in an adjacent fluid channel 140, and so on across array 110. Alternatively, compositional variation can be introduced by varying the concentration of a conductive or semiconductive organic material in a composite sensor across fluid channels. In still another variation, a variety of different organic materials may be used in sensors in different channels. Similar patterns of introducing compositional variation into sensor arrays 110 will be readily apparent to those skilled in the art.

Although FIG. 1 illustrates fluid channels 130, 140 as linear channels extending in just one direction, sensor arrays can be configured to provide similar fluid channels having different geometries—for example, arrays with sensors arranged in two or more directions relative to the fluid flow, such as a circular array having a radial arrangement of sensors around a fluid introduction point. And although sensor array 110 has been described as incorporating one or more fluid channels each comprising a plurality of nominally identical sensors, those skilled in the art will recognize that the techniques described herein can be used to generate useful spatio-temporal information from arrays including a plurality of sensors all of different chemistry, structure or composition, with the fluid path being defined by the introduction of the fluid onto the array. In this implementation, spatio-temporal response data can be generated by introducing the fluid onto the array at varying flow rates, for example, by using a flow controller of known construction to systematically vary the rate at which the fluid is introduced over time. Alternatively, flow rate variation can be introduced by simply exposing the array to a naturally varying fluid flow, such as a flow of air.

A system 100 is fabricated by electrically coupling the sensor leads of an array of differently responding sensors to an electrical measuring device 180. The device measures changes in signal at each sensor of the array, preferably simultaneously and preferably over time. The signal is an electrical resistance, impedance or other physical property of the material in response to the presence of the analyte in the fluid. Frequently, the device 180 includes signal processing means and is used in conjunction with a computer and data structure for comparing a given response profile to a structure-response profile database for qualitative and quantitative analysis. Typically an array 110 for use in system 100 comprises usually at least ten, often at least 100, and perhaps at least 1000 different sensors though with mass deposition fabrication techniques described herein or otherwise known in the art, arrays of on the order of at least one million sensors are readily produced.

In one mode of operation with an array of sensors, each sensor provides a first electrical signal when the sensor is contacted with a first fluid comprising a first chemical analyte, and a second electrical signal between its conductive leads when the sensor is contacted with a second fluid comprising a second, different chemical analyte. The fluids may be liquid or gaseous in nature. The first and second fluids may reflect samples from two different environments, a change in the concentration of an analyte in a fluid sampled at two time points, a sample and a negative control, etc. The sensor array necessarily comprises sensors that respond differently to a change in an analyte concentration or identity, i.e., the difference between the first and second electrical signal of one sensor is different from the difference between the first and second electrical signals of another sensor.

In one embodiment, the temporal response of each sensor (for example, signal as a function of time) is recorded. The temporal response of each sensor can be normalized to a maximum percent increase and percent decrease in signal that produces a response pattern associated with the exposure of the analyte. By iterative profiling of known analytes, a structure-function database correlating analytes and response profiles is generated. Unknown analytes can then be characterized or identified using response pattern comparison and recognition algorithms. Accordingly, analyte detection systems comprising sensor arrays, an electrical measuring device for detecting signal at each sensor, a computer, a data structure of sensor array response profiles, and a comparison algorithm are provided. In another embodiment, the electrical measuring device is an integrated circuit comprising neural network-based hardware and a digital-analog converter (DAC) multiplexed to each sensor, or a plurality of DACs, each connected to different sensor(s).

The desired signals if monitored as dc electrical resistances for the various sensor elements in an array can be read merely by imposing a constant current source through the resistors and then monitoring the voltage across each resistor through use of a commercial multiplexable 20 bit analogto-digital converter. Such signals are readily stored in a computer that contains a resident algorithm for data analysis and archiving. Signals can also be preprocessed either in digital or analog form; the latter might adopt a resistive grid configuration, for example, to achieve local gain control. In addition, long time adaptation electronics can be added or the data can be processed digitally after it is collected from the sensors themselves. This processing could be on the same chip as the sensors but also could reside on a physically separate chip or computer.

Data analysis can be performed using standard chemometric methods such as principal component analysis and SIMCA, which are available in commercial software packages that run on a PC or which are easily transferred into a computer running a resident algorithm or onto a signal analysis chip either integrated onto, or working in conjunction with, the sensor measurement electronics. The Fisher linear discriminant is one preferred algorithm for analysis of the data, as described below. In addition, more sophisticated algorithms and supervised or unsupervised neural network based learning/training methods can be applied as well (Duda, R. O.; Hart, P. E. Pattern Classification and Scene Analysis; John Wiley & Sons: New York, 1973, pp 482).

The signals can also be useful in forming a digitally transmittable representation of an analyte in a fluid. Such signals could be transmitted over the Internet in encrypted or in publicly available form and analyzed by a central processing unit at a remote site, and/or archived for compilation of a data set that could be mined to determine, for example, changes with respect to historical mean "normal" values of the breathing air in confined spaces, of human breath profiles, and of a variety of other long term monitoring situations where detection of analytes in fluids is an important value-added component of the data.

An array of 20–30 different sensors is sufficient for many analyte classification tasks but larger array sizes can be implemented as well. Temperature and humidity can be controlled but because a preferred mode is to record changes relative to the ambient baseline condition, and because the patterns for a particular type and concentration of odorant are generally independent of such baseline conditions, it is not critical to actively control these variables in some implementations of the technology. Such control could be achieved either in open-loop or closed-loop configurations.

The sensor arrays disclosed herein could be used with or without preconcentration of the analyte depending on the power levels and other system constraints demanded by the user. Regardless of the sampling mode, the characteristic patterns (both from amplitude and temporal features, depending on the most robust classification algorithm for the purpose) associated with certain disease states and other volatile analyte signatures can be identified using the sensors disclosed herein. These patterns are then stored in a library, and matched against the signatures emanating from the sample to determine the likelihood of a particular odor falling into the category of concern (disease or nondisease, toxic or nontoxic chemical, good or bad polymer samples, fresh or old fish, fresh or contaminated air etc.).

Analyte sampling will occur differently in the various application scenarios. For some applications, direct headspace samples can be collected using either single breath and urine samples in the case of sampling a patient's breath for the purpose of disease or health state differentiation and classification. In addition, extended breath samples, passed over a Tenax, Carbopack, Poropak, Carbosieve, or other sorbent preconcentrator material, can be obtained when needed to obtain robust intensity signals. The absorbent material of the fluid concentrator can be, but is not limited to, a nanoporous material, a microporous material, a chemically reactive material, a nonporous material and combinations thereof. In certain instances, the absorbent material can concentrate the analyte by a factor that exceeds a factor of about $10^5$, or by a factor of about $10^2$ to about $10^4$. In another embodiment, removal of background water vapor is conducted in conjunction, such as concomitantly, with the concentration of the analyte. Once the analyte is concentrated, it can be desorbed using a variety of techniques, such as heating, purging, stripping, pressuring or a combination thereof.

Breath samples can be collected through a straw or suitable tube in a patient's mouth that is connected to the sample chamber (or preconcentrator chamber), with the analyte outlet available for capture to enable subsequent GC/MS or other selected laboratory analytical studies of the sample. In other applications, headspace samples of odorous specimens can be analyzed and/or carrier gases can be used to transmit the analyte of concern to the sensors to produce the desired response. In still other cases, the analyte will be in a liquid phase and the liquid phase will be directly exposed to the sensors; in other cases the analyte will undergo some separation initially and in yet other cases only the headspace of the analyte will be exposed to the sensors.

Using the device of the present invention, the analyte can be concentrated from an initial sample volume of about 10 liters and then desorbed into a concentrated volume of about 10 milliliters or less, before being presented to the sensor array.

Suitable commercially available adsorbent materials include but are not limited to, Tenax TA, Tenax GR, Carbotrap, Carbopack B and C, Carbotrap C, Carboxen, Carbosieve SIII, Porapak, Spherocarb, and combinations thereof. Preferred adsorbent combinations include, but are not limited to, Tenax GR and Carbopack B; Carbopack B and Carbosieve SIII; and Carbopack C and Carbopack B and Carbosieve SIII or Carboxen 1000. Those skilled in the art will know of other suitable absorbent materials.

In another embodiment, removal of background water vapor is conducted in conjunction, such as concomitantly, with the concentration of the analyte. Once the analyte is concentrated, it can be desorbed using a variety of techniques, such as heating, purging, stripping, pressuring or a combination thereof. In these embodiments, the sample concentrator is wrapped with a wire through which current can be applied to heat and thus, desorb the concentrated analyte. The analyte is thereafter transferred to the sensor array.

In some cases, the array will not yield a distinct signature of each individual analyte in a region, unless one specific type of analyte dominates the chemical composition of a sample. Instead, a pattern that is a composite, with certain characteristic temporal features of the sensor responses that aid in formulating a unique relationship between the detected analyte contents and the resulting array response, will be obtained.

In a preferred embodiment of signal processing, the Fisher linear discriminant searches for the projection vector, w, in the detector space that maximizes the pairwise resolution factor, i.e., rf, for each set of analytes, and reports the value of rf along this optimal linear discriminant vector. The rf value is an inherent property of the data set and does not depend on whether principal component space or original detector space is used to analyze the response data. This resolution factor is basically a multi-dimensional analogue to the separation factors used to quantify the resolving power of a column in gas chromatography, and thus the rf value serves as a quantitative indication of how distinct two patterns are from each other, considering both the signals and the distribution of responses upon exposure to the analytes that comprise the solvent pair of concern. For example, assuming a Gaussian distribution relative to the mean value of the data points that are obtained from the responses of the array to any given analyte, the probabilities of correctly identifying an analyte as a or b from a single presentation when a and b are separated with resolution factors of 1.0, 2.0 or 3.0 are approximately 76%, 92% and 98% respectively.

To compute the rf, from standard vector analysis, the mean response vector, $x_a$, of an n-sensor array to analyte a is given as the n-dimensional vector containing the mean autoscaled response of each sensors, $A_{aj}$, to the $a^{th}$ analyte as components such that $$x_a = (A_{a1}, A_{a2}, \ldots A_{an})$$

The average separation, $|d|$, between the two analytes, a and b, in the Euclidean sensor response space is then equal to the magnitude of the difference between $x_a$ and $x_b$. The noise of the sensor responses is also important in quantifying the resolving power of the sensor array. Thus the standard deviations, $s_{a,d}$ and $s_{b,d}$, obtained from all the individual array responses to each of a and b along the vector d, are used to describe the average separation and ultimately to define the pairwise resolution factor as $$rf = d_w / \sqrt{(\sigma^2_{a,w} + \sigma^2_{b,w})}.$$

Even if the dimensionality of odor space is fairly small, say on the order of $10^1$, there is still interest in being able to model the biological olfactory system in its construction of arrays consisting of large numbers of receptor sites. Furthermore, even if a relatively small number (<10) of ideal sensors could indeed span odor space, it is not likely that such ideal sensors could be identified. In practice, correlations between the elements of a sensor array will necessitate a much larger number of sensors to successfully distinguish molecules. Furthermore, performance issues such as response time, signal averaging, or calibration ranges may require multiple sensors based on each material. Analysis of regions will add additional degrees of freedom if the components of the region are to be individually identified and will require large numbers of sensors. Fabrication of large numbers of sensors also enables the use of very powerful coherent signal detection algorithms to pull a known, but small amplitude, signal, out of a noisy background. Because of all of these issues, the number of sensors required to successfully span odor space in a practical device may rapidly multiply from the minimum value defined by the dimensionality of smell space.

The sensor arrays disclosed herein act as "electronic noses" to offer ease of use, speed, and identification of analytes and/or analyte regions all in a portable, relatively inexpensive implementation. A wide variety of analytes and fluids may be analyzed by the disclosed arrays so long as the subject analyte is capable generating a differential response across a plurality of sensors of the array. Analyte applications include broad ranges of chemical classes such as organics including, for example, alkanes, alkenes, alkynes, dienes, alicyclic hydrocarbons, arenes, alcohols, ethers, ketones, aldehydes, carbonyls, carbanions, biogenic amines, thiols, polynuclear aromatics and derivatives of such organics, e.g., halide derivatives, etc., biomolecules such as sugars, isoprenes and isoprenoids, fatty acids and derivatives, etc.

Commercial applications of the arrays include environmental toxicology and remediation, materials quality control, food and agricultural products monitoring, fruit ripening control, fermentation process monitoring and control applications, flavor composition and identification, cosmetic/perfume/fragrance formulation, anaesthetic detection, ambient air quality monitoring, emissions monitoring and control, leak detection and identification, $H_2S$ monitoring, automobile oil or radiator fluid monitoring, hazardous spill identification, fugitive emission identification, medical diagnostics, detection and classification of bacteria and microorganisms both in vitro and in vivo for biomedical uses and medical diagnostic uses, infectious disease detection, body fluids analysis, drug discovery, telesurgery, breath alcohol analyzers, illegal substance detection and identification, arson investigation, smoke and fire detection, combustible gas detection, explosives and chemical weapons detection and identification, enclosed space surveying, personal identification, automatic ventilation control applications (cooking, smoking, etc.), air intake monitoring, and the like.

The following examples are offered by way of illustration and not by way of limitation.

EXAMPLES

In the following examples, broadly responsive sensor arrays were constructed based on carbon black composites for various vapor detection tasks. Individual sensor elements were constructed from films consisting of carbon black particles dispersed into insulating organic polymers. The carbon black endows electrical conductivity to the films, whereas the different organic polymers are the source of chemical diversity between elements in the sensor array. Swelling of the polymer upon exposure to a vapor increases the resistance of the film, thereby providing an extraordinarily simple means for monitoring the presence of a vapor. Because different polymer compositions are present on each sensor element, an array of elements responds to a wide variety of vapors (or complex mixtures of vapors) in a distinctive, identifiable fashion. The electrical resistance signals that are output from the array can be readily integrated into software- or hardware-based decision systems, allowing for an integration of sensing and analysis functions into a compact, low-power, simple vapor sensor.

Preparation of Sensor Arrays.

In general, arrays of nominally identical polymer-carbon black composite sensors were constructed by spray-coating a ceramic substrate having pairs of leads spaced 1.0 mm apart. Each sensor was sprayed from a suspension of carbon black in a solvent that dissolved the polymer, and the components had a weight percentage of 20% of carbon black to dissolved polymer. The leads were 3.5 mm in length and 0.1 mm in width and were interdigitated such that the total width contacting a given sensor film was 3.0 mm. The output of every pair of leads from each sensor were connected to a printed circuit board equipped with electronics that read the resistance signals to a precision of <5 ppm every 0.5 s on the entire bank of sensors.

Example 1

Referring to FIG. 3, an array 300 of eight nominally identical poly(methyloctadecylsiloxane)-carbon black composite sensors 301–308 was constructed as described above.

A stream 310 of 2,4-dinitrotoluene (DNT) in air at 5% of its vapor pressure was directed onto the surface, such that the stream was directed at sensor 304 and then moved radially in both directions across the array.

5% of the vapor pressure of DNT at 20° C. was selected as a dilution of DNT that would deliver less than 10 ppb of the compound to the sensors. The DNT source was a tube approximately a meter in length that held about 180 g of loosely packed, granulated DNT. The air flow through the tube was 0.5 L-min$^{-1}$. This air flow was mixed with, and therefore diluted by a flow of 9.5 L-min$^{-1}$ of air (from the same source) that did not flow through the DNT tube. At this dilution, the upper limit of the DNT concentration is 7 ppb, because the vapor pressure of DNT at room temperature is approximately 140 ppb. If saturation of the background air through the DNT tube occurred, and if no DNT stuck to the walls of the tubing after mixing with the pure background analyte flow, this dilution would produce a concentration of 7 ppb of DNT. However, analyses performed by sorbing the analyte flow onto Tenax for a 10 minute period (to obtain enough DNT with which to perform analysis) and then analyzing the desorbed products with a GC-ECD system indicated that the actual DNT concentration exiting the tubing and available to be detected was approximately 0.2–0.4 ppb.

Flows were controlled by mass flow controllers in a computer controlled system that has been described in detail in Severin, E. J., Doleman, B. J., Lewis, N. S., *Anal. Chem.*, 2000, 72, 658. A union-T was used to mix the background and analyte-containing gases, and a short Teflon tube was connected to the output of the union to direct the gas toward the bank of sensors. The array substrate was placed such that the sensors were perpendicular to the output of the DNT flow and were approximately 0.5 cm from the end of the tubing.

The DNT flow was delivered at four flow rates: 0.5 liters/min, 1.0 liters/min, 3.0 liters/min and 6.0 liters/min. Results reporting the sensor response as a function of time for the eight sensors are plotted in FIGS. 4*a*–*b*. Sensor 304, in the center of the array and directly under the flow, responds faster and to a greater extent for each of the tested flow rates. The flow rate dependence of the response for this sensor is illustrated in FIGS. 5*a*–*b*, which depict the slope of the response for sensor 304 as a function of flow rate.

Example 2

Referring to FIG. 6, an array 600 of eight nominally identical poly(ethylene-co-vinylacetate)-carbon black composite sensors 601–608 was prepared in a row on a single ceramic substrate as described above. An aluminum plate 610 was placed over the substrate, separated from the substrate surface by narrow Teflon spacers to create a small channel approximately 5 mm wide and 70 microns high over the row of sensors, with openings 615, 620 at either end. The substrate assembly was placed in a Teflon chamber 630 of dimensions approximately 5 cm by 5 cm by 10 cm. A stream of air was directed through the Teflon chamber. Flows were controlled as described in Severin, E. J., Doleman, B. J., Lewis, N. S., *Anal. Chem.*, 2000, 72, 658. During times of exposure, this stream also contained one of the four analytes at 5% of its vapor pressure. Four analytes covering a range of vapor pressures were used to study the response characteristics: n-dodecane, n-nonane, methanol, and n-hexane. The total flow into the chamber was maintained constant at all times.

The ΔR/R response was calculated using data averaged over five second periods. The baseline resistance, R, was taken from the period immediately before starting the vapor presentation and the value of ΔR/R was taken as the difference in resistance after 300 seconds of vapor presentation and the baseline resistance. This response was calculated for each of the eight sensor positions.

The spatial dependence of sensor responses to these analytes at each of the eight sensors is shown in FIG. 7. The high vapor pressure analytes produced equilibrium responses of similar magnitude on all of the sensors. By contrast, the lower vapor pressure analytes (n-nonane and n-dodecane) produced higher magnitude responses on the sensors near the openings than on the sensors in the middle of the channel.

Example 3

An array 300 of eight nominally identical poly(methyloctadecylsiloxane)-carbon black composite sensors 301–308 was constructed as described above and configured as described in Example 1.

The experimental protocol consisted of one hour of exposure to air only, followed by ten control exposures to 5 s DNT pulses spaced every 605 s, followed by a randomized sequence of 20 exposures/nonexposures to DNT spaced every 605 s. The data were then analyzed independently without knowledge of the actual order of the randomized sequence of exposures/nonexposures.

A run was also performed to investigate whether responses would be obtained due to small changes in the flow rate of gas to the sensors. For this experiment, the existing lines were unhooked at the outlets of both mass flow controllers (the one feeding the DNT generator and the one providing diluent air). The lines were then replaced with lines and a union-T that had never been exposed to DNT or to solvents. The lengths of the flow paths with the new lines in place approximated those in the DNT dilution system. A run of four 60 s exposures, each separated by 10 min, was performed. In this run, 5% of the air during each exposure came via the mass flow controller that was normally used to feed the DNT generator. The total flow rate at all times was 10 L-min$^{-1}$.

FIG. 8 shows the resistance (in units of 10 kΩ) versus time profile computed by averaging over the bank of eight nominally identical poly(methyloctadecylsiloxane)-carbon black sensors that were placed perpendicular to the outlet of the DNT flow. The vertical lines show the ground truth of when the DNT puffs were applied. The first ten lines represent the control set. Note that the time axis spans over 6 hours (22,000 s). The series of "bumps" that are visible on this long time scale plot are not related to the DNT pulses, and in fact represent environmentally-induced oscillations in the baseline resistance of the sensor. The DNT-induced behavior occurs on a 5 second time scale that is not discernible on this plot.

FIG. 9 plots sensor output versus time over the 6+ hours of the experiment. The vertical lines show the ground truth of when DNT puffs were applied. The units on the y-axis are in standard deviations of the signal relative to the local background of the sensor. As shown in FIG. 9, using essentially a matched filter algorithm with adaptive background subtraction, all DNT exposures and non-exposures were correctly identified within the randomized sequence. The black circles show local maxima of the sensor output that exceeded a given threshold. Based on this selection criterion, all of the DNT exposures were detected with no false alarms. In fact, a much stronger result was obtained: the separability at the sensor output was sufficient for all DNT exposures (in the control set and the randomized set) to be correctly identified with zero false alarms over the entire >6 hour duration of the experiment.

The highest sensor output value (15.3) occurred at the 6th control sample. The resistance versus time profile for this sample is shown in detail in FIG. 10a. The sensor output versus time is shown in FIG. 10b. An intermediate case (roughly the median in sensor output fidelity) occurred at the 4th control sample. The resistance versus time profile for this sample is shown in detail in FIG. 11a. The sensor output versus time is shown in FIG. 11b. The lowest sensor output value (7.35) occurred at the 7th control sample. The resistance versus time profile for this sample is shown in detail in FIG. 12a. The sensor output versus time is shown in FIG. 12b.

Although all the DNT exposures were perfectly separated from the background with zero false alarms, it is interesting to look at the "close calls" or "near false alarms". In FIG. 9 there are 4 places where the sensor output on the background exceeds a threshold of 5 but is still well below the minimum target value of 7.35. The detailed resistance versus time profiles for 2 of these 4 "near false alarms" are shown in FIGS. 13a–b.

Example 4

A separate set of experiments was performed to evaluate the dependence of DNT detection on the flow rate of DNT to the sensors. For this run, a poly(methyloctadecylsiloxane)-carbon black mixture was spray-coated onto the edges of glass slides. Prior to the deposition of the sensor film, conductive coatings had been deposited onto both surfaces of the slides. Spacers were then placed between these edge-coated slides. The result was a sensor with a width of ≈6 mm that had slits 0.13–0.25 mm in width spanning the length of the sensor. This ventilated sensor assembly was then cemented into one end of a section of vacuum hose. The other end of the hose was connected to a vacuum pump. A flow meter was placed in the line to monitor the flow rate through the slits in the sensor. The rectangular sensor face was fitted into a similarly-sized aperture in a Teflon block, the fit being loose enough that gas flow onto the sensor could escape around the edges. The output tube of the gas mixer was fitted to a second teflon block that was bolted to the block holding the sensor assembly, creating a small chamber with a volume of about 0.3 cm$^3$. The resulting distance between the gas mixture outlet and the sensor was ≈5 mm. The resistance of the sensor was measured by connecting the leads to one channel in a data acquisition board that recorded the resistance versus time data. The data were then transferred to a laptop computer.

Four trials were performed, with each trial using vapor emerging from the DNT-containing analyte tube diluted to 5% by volume with background air. In experiment 1, 10 exposures were made following a 20 min purge with air at 10 L-min$^{-1}$. Each DNT exposure was 10 s in length. The total flow rates into the sensor chamber were varied progressively, starting at 1 L-min$^{-1}$ for the first exposure and ending with an exposure at 10 L-min. Each exposure was followed by a purge at 10 L-min$^{-1}$ of background air. Prior to each exposure, the flow through the vacuum line drawing gas through the sensor was set to produce a flow rate that was 1 L-min$^{-1}$ less than the flow rate impinging onto the sensor chamber. This positive differential flow rate arrangement was used to avoid drawing in ambient air through the remaining gap between the sensor and the walls of the chamber.

In experiment 2, 10 exposures were made using the same ascending series of total flow rates into the chamber (i.e. 1–10 L-min$^{-1}$), but no vacuum was applied during any of the exposures.

In experiment 3, the same ascending series of flow rates into the chamber was used, and the same ascending series of vacuum-induced flow rates through the sensor as in experiment 1 was employed, but no analyte (DNT) was present.

In experiment 4, the flow rate of DNT (at 5% of its vapor pressure at 20° C.) into the chamber as not varied, being maintained at 10 L-min$^{-1}$ for all 10 exposures. Vacuum-induced flow rates through the sensor were, however, varied in the same way as in experiments 1 and 3, beginning with no flow for the first exposure and ending with 9 L-min$^{-1}$ during the 10$^{th}$ and final exposure.

FIG. 14a–b illustrates the dependence of signal from the ventilated sensor on flow rate with the flow rate varying from 1 to 10 liters/min. FIG. 14a shows resistance transients for a 1 minute exposure of DNT at 5% of its vapor pressure (top: vacuum on; bottom: vacuum off). FIG. 14b shows the change in resistance as a function of time indicating magnitude of slope during exposure. As these figures illustrate, pulling analyte through the sensor at a rate about 1 L-min$^{-1}$ less than the flow rate of gas into the chamber generally resulted in an increase in sensor response of a factor of 2. This was particularly noticeable at higher flow rates. When flow into the sensor chamber was kept at a constant, high rate (10 L-min$^{-1}$), the sensor response increased, apparently due to increased flow through the sensor slits.

The ventilated sensor response characteristics for 5 s exposures to 10 L-min$^{-1}$ total flow rates of 5% DNT as a function of flow rate through the sensor are illustrated in FIGS. 15a–c. FIG. 15a shows response transients ranging from no flow through the sensor (second from the bottom) to 9 L-min-1 through the sensor (top). FIG. 15b shows response slope as a function of flow rate through the sensor. FIG. 15c shows signal to noise after 5 s exposure as a function of flow rate.

Although only a few embodiments have been described in detail above, those having ordinary skill in the art will certainly understand that many modifications are possible in the preferred embodiment without departing from the teachings thereof. All such modifications are intended to be encompassed within the following claims.

What is claimed is:

1. A system for identifying an analyte in a fluid, comprising:
    a fluid flow chamber having a first end and a second end;
    a sensor array including at least a first sensor and a second sensor in an arrangement in the fluid flow chamber such that at least the first sensor is proximal to the first end of the flow chamber and at least the second sensor is proximal to the second end of the flow chamber thereby having a defined fluid flow path, wherein a fluid moving in the fluid flow chamber contacts the at least two sensors at different times;
    a measuring apparatus coupled to the sensor array, the measuring apparatus being configured to detect a response from the first sensor and the second sensor upon exposure of the sensor array to the fluid; and
    a computer configured to generate data indicating the analyte in the fluid based on a spatio-temporal difference between the responses for the first and second sensors and identifying the analyte based upon the spatio-temporal difference.

2. The system of claim 1, wherein:

the data includes a spatio-temporal response profile derived from the spatio-temporal difference between the responses for the first and second sensors.

3. The system of claim 2, wherein:

the spatio-temporal response profile is derived from time information indicating the dependence of sensor response on time.

4. The system of claim 3, wherein:

the first sensor occupies a first position in the arrangement and the second sensor occupies a second position in the arrangement, such that the response of the second sensor is delayed in time with respect to the response of the first sensor upon exposure of the sensor array to the fluid.

5. The system of claim 3, wherein:

the first sensor occupies a first position in the arrangement and the second sensor occupies a second position in the arrangement, such that the response of the second sensor is changed in amplitude with respect to the response of the first sensor upon exposure of the sensor array to the fluid.

6. The system of claim 5, wherein:

the first sensor includes a sensing material; and the response of the first sensor is greater than the response of the second sensor for an analyte having a high affinity for the sensing material.

7. The system of claim 4, wherein:

the first and second sensors are selected and arranged to provide a first delay between the response of the first sensor and the response of the second sensor upon exposure of the sensor array to a fluid including a first analyte and a second delay between the response of the first sensor and the response of the second sensor upon exposure of the sensor array to a fluid including a second analyte.

8. The system of claim 7, wherein:

the measuring apparatus is configured to measure the delay between the response of the first sensor and the response of the second sensor; and the spatio-temporal difference between the responses for the first and second sensors is derived from the delay.

9. The system of claim 8, wherein:

the computer is configured to characterize the analyte based on the spatio-temporal difference between the responses.

10. The system of claim 2, further comprising:

a flow controller to introduce the fluid to the sensor array at a varying flow rate.

11. The system of claim 10 wherein:

the computer is configured to generate flow information indicating the dependence of sensor response on flow rate.

12. The system of claim 2, wherein:

the sensor array includes a plurality of cross-reactive sensors.

13. The system of claim 2, wherein:

the sensor array includes a plurality of sensors selected from the group including surface acoustic wave sensors, quartz crystal resonators, metal oxide sensors, dye-coated fiber optic sensors, dye-impregnated bead arrays, micromachined cantilever arrays, composites having regions of conducting material and regions of insulating organic material, composites having regions of conducting material and regions of conducting or semiconducting organic material, chemically-sensitive resistor or capacitor films, metal-oxide-semiconductor field effect transistors, and bulk organic conducting polymeric sensors.

14. The system of claim 2, wherein:

the first and second sensors comprise composites having regions of a conducting material and regions of an insulating organic material.

15. The system of claim 2, wherein:

the first and second sensors comprise composites having regions of a conducting material and regions of a conducting organic material.

16. The system of claim 2, wherein:

the computer is configured to generate a digital representation of the analyte based at least in part on the responses of the first and second sensors.

17. The system of claim 16, further comprising:

a communications port coupled to the computer for communicating the digital representation of the analyte to a remote location for analysis.

18. A system for detecting an analyte in a fluid, comprising:

a sensor array including a first sensor and a second sensor;

a fluid flow chamber comprising a fluid inlet proximate to the first sensor of the sensor array, and wherein the second sensor is further distal to the fluid inlet thereby defining a fluid flow pattern such that the first and second sensors are located at different locations in the sensor array relative to the fluid flow pattern, wherein a fluid moving in the defined fluid flow pattern contacts the at least two sensors at different times;

a measuring apparatus connected to the sensor array, the measuring apparatus being configured to detect a response from the first sensor and the second sensor upon exposure of the sensor array to the fluid, the responses for the first and second sensors based on the locations of the sensors relative to the fluid flow pattern; and a computer configured to generate data indicating the analyte in the fluid based on a spatio-temporal difference between the responses for the first and second sensors and identifying the analyte based upon the spatio-temporal difference.

19. The system of claim 18, wherein:

the spatio-temporal difference is derived from time information indicating the dependence of sensor response on time.

20. The system of claim 19, wherein:

the first sensor occupies a first position relative to the fluid flow pattern and the second sensor occupies a second position relative to the fluid flow pattern, such that the response of the second sensor is delayed with respect to the response of the first sensor upon exposure of the sensor array to the fluid.

21. The system of claim 19, wherein:

the first sensor occupies a first position relative to the fluid flow pattern and the second sensor occupies a second position relative to the fluid flow pattern, such that the response of the second sensor is changed in amplitude with respect to the response of the first sensor upon exposure of the sensor array to the fluid.

22. The system of claim 21, wherein:

the first sensor includes a sensing material; and the response of the first sensor is greater than the response of the second sensor for an analyte having a high affinity for the sensing material.

23. The system of claim 20, wherein:

the first and second sensors are selected and arranged to provide a first delay between the response of the first sensor and the response of the second sensor upon exposure of the sensor array to a fluid including a first analyte and a second delay between the response of the first sensor and the response of the second sensor upon exposure of the sensor array to a fluid including a second analyte.

24. The system of claim 23, wherein:

the measuring apparatus is configured to measure the delay between the response of the first sensor and the response of the second sensor; and the spatio-temporal difference between the responses for the first and second sensors is derived from the delay.

25. The system of claim 19, further comprising:

a computer configured to characterize the analyte based on the spatio-temporal difference between the responses.

26. The system of claim 18, further comprising:

a flow controller to introduce the fluid to the sensor array at a varying flow rate.

27. The system of claim 26, wherein:

the measuring apparatus is configured to measure flow information indicating the dependence of sensor response on flow rate.

28. The system of claim 18, wherein:

the sensor array includes a plurality of cross-reactive sensors.

29. The system of claim 18, wherein:

the sensor array includes a plurality of sensors selected from the group including surface acoustic wave sensors, quartz crystal resonators, metal oxide sensors, dye-coated fiber optic sensors, dye-impregnated bead arrays, micromachined cantilever arrays, composites having regions of conducting material and regions of insulating organic material, composites having regions of conducting material and regions of conducting or semiconducting organic material, chemically-sensitive resistor or capacitor films, metal-oxide-semiconductor field effect transistors, and bulk organic conducting polymeric sensors.

30. The system of claim 18, wherein:

the first and second sensors comprise composites having regions of a conducting material and regions of an insulating organic material.

31. The system of claim 18, wherein:

the first and second sensors comprise composites having regions of a conducting material and regions of a conducting organic material.

32. The system of claim 25, wherein:

the computer is configured to generate a digital representation of the analyte based at least in part on the responses of the first and second sensors.

33. A system for detecting an analyte in a fluid, comprising:

a sensor array including a first sensor and a second sensor;

a fluid flow chamber comprising a first end and a second end, whereby the first and second sensors occupy different locations in the sensor array relative to the first end and second end of the fluid flow chamber, wherein a fluid moving in a defined fluid flow path contacts the at least two sensors at different times;

a measuring apparatus connected to the sensor array, the measuring apparatus being configured to detect a response from the first and second sensor upon exposure of the sensor array to the fluid flow, the response differences based on the locations of the sensors in the sensor array relative to the fluid flow; and a computer configured to generate data indicating the analyte in the fluid based on a spatio-temporal difference between the responses for the first and second sensors and identifying the analyte based upon the spatio-temporal difference.

34. The system of claim 33, wherein:

the spatio-temporal difference is derived from time information indicating the dependence of sensor response on time.

35. The system of claim 34, wherein:

the first sensor occupies a first position relative to the fluid flow and the second sensor occupies a second position relative to the fluid flow, such that the response of the second sensor is delayed with respect to the response of the first sensor upon exposure of the sensor array to the fluid.

36. The system of claim 34, wherein:

the first sensor occupies a first position relative to the fluid flow and the second sensor occupies a second position relative to the fluid flow, such that the response of the second sensor is changed in amplitude with respect to the response of the first sensor upon exposure of the sensor array to the fluid.

37. The system of claim 36, wherein:

the first sensor includes a sensing material; and the response of the first sensor is greater than the response of the second sensor for an analyte having a high affinity for the sensing material.

38. The system of claim 35, wherein:

the first and second sensors are selected and arranged to provide a first delay between the response of the first sensor and the response of the second sensor upon exposure of the sensor array to a fluid including a first analyte and a second delay between the response of the first sensor and the response of the second sensor upon exposure of the sensor array to a fluid including a second analyte.

39. The system of claim 38, wherein:

the measuring apparatus is configured to measure the delay between the response of the first sensor and the response of the second sensor; and the spatio-temporal difference between the responses for the first and second sensors is derived from the delay.

40. The system of claim 33, further comprising:

a computer configured to characterize the analyte based on the spatio-temporal difference between the responses.

41. The system of claim 33, further comprising:

a flow controller to vary the rate of the fluid flow.

42. The system of claim 41, wherein:

the measuring apparatus is configured to measure flow information indicating the dependence of sensor response on flow rate.

43. The system of claim 33, wherein:

the sensor array includes a plurality of cross-reactive sensors.

44. The system of claim 33, wherein:

the sensor array includes a plurality of sensors selected from the group including surface acoustic wave sensors, quartz crystal resonators, metal oxide sensors, dye-coated fiber optic sensors, dye-impregnated bead arrays, micromachined cantilever arrays, composites having regions of conducting material and regions of insulating organic material, composites having regions of conducting material and regions of conducting or semiconducting organic material, chemically-sensitive resistor or capacitor films, metal-oxide-semiconductor field effect transistors, and bulk organic conducting polymeric sensors.

45. The system of claim 33, wherein:

the first and second sensors comprise composites having regions of a conducting material and regions of an insulating organic material.

46. The system of claim 33, wherein:

the first and second sensors comprise composites having regions of a conducting material and regions of a conducting organic material.

47. The system of claim 40, wherein:

the computer is configured to generate a digital representation of the analyte based at least in part on the responses of the first and second sensors.

* * * * *